United States Patent
Yang et al.

(10) Patent No.: US 12,274,803 B2
(45) Date of Patent: Apr. 15, 2025

(54) SYSTEMS AND METHODS FOR SANITIZING MOBILE ELECTRONIC DEVICES

(71) Applicant: simplehuman, LLC, Torrance, CA (US)

(72) Inventors: Frank Yang, Rancho Palos Verdes, CA (US); Ryan Wong, Long Beach, CA (US); Cory Bowman, Mission Viejo, CA (US); Frederick Bushroe, Tucson, AZ (US); William Patrick Conley, Long Beach, CA (US); Nasser Pirshafiey, Trabuco Canyon, CA (US)

(73) Assignee: simplehuman, LLC, Torrance, CA (US)

( * ) Notice: Subject to any disclaimer, the term of this patent is extended or adjusted under 35 U.S.C. 154(b) by 0 days.

(21) Appl. No.: 18/425,218

(22) Filed: Jan. 29, 2024

(65) Prior Publication Data

US 2024/0307570 A1    Sep. 19, 2024

Related U.S. Application Data

(63) Continuation of application No. 17/444,255, filed on Aug. 2, 2021, now Pat. No. 11,918,697.
(Continued)

(51) Int. Cl.
    *A61L 2/10*    (2006.01)
    *A61L 2/26*    (2006.01)

(52) U.S. Cl.
    CPC ............... *A61L 2/10* (2013.01); *A61L 2/26* (2013.01); *A61L 2202/11* (2013.01); *A61L 2202/122* (2013.01)

(58) Field of Classification Search
    CPC .......... A61L 2/10; A61L 2/26; A61L 2202/11; A61L 2202/122
    See application file for complete search history.

(56) References Cited

U.S. PATENT DOCUMENTS

| 8,964,405 B2 | 2/2015 | La Porte et al. |
| 9,339,576 B2 | 5/2016 | La Porte et al. |

(Continued)

FOREIGN PATENT DOCUMENTS

| CN | 111214685 A | 6/2020 |
| CN | 111265687 A | 6/2020 |

(Continued)

*Primary Examiner* — Sean M Luck
(74) *Attorney, Agent, or Firm* — Knobbe, Martens, Olson & Bear, LLP

(57) ABSTRACT

This disclosure includes a description of a sanitizing system for sanitizing a mobile electronic device comprising: a housing; a sanitizer contained within the housing configured to emit radiation with a sanitizing effect; and an entry system with a default closed position, the entry system being configured to permit a mobile electronic device to pass through the entry system and then automatically return to the default closed position, the entry system comprising a first outer enclosure and a second inner obstruction; wherein the entry system blocks radiation emitted within the sanitizing system to a level acceptable for consumer use, or wherein the second inner obstruction provides more radiation attenuation than the first outer enclosure, and/or wherein the combination of the first outer enclosure and the second inner obstruction provides more radiation attenuation than the first outer enclosure by itself. Disclosed are internal reflectors to help distribute sanitizing radiation generally evenly.

20 Claims, 27 Drawing Sheets

Related U.S. Application Data

(60) Provisional application No. 63/125,942, filed on Dec. 15, 2020, provisional application No. 63/090,054, filed on Oct. 9, 2020, provisional application No. 63/060,566, filed on Aug. 3, 2020.

(56)  References Cited

U.S. PATENT DOCUMENTS

| | | |
|---|---|---|
| 10,744,215 B2 | 1/2020 | La Porte et al. |
| 11,033,645 B1 | 6/2021 | Mora et al. |
| 11,918,697 B2 | 3/2024 | Yang et al. |
| 2010/0044582 A1 | 2/2010 | Cooper et al. |
| 2013/0063922 A1 | 3/2013 | La Porte et al. |
| 2013/0277574 A1 | 10/2013 | Dayton |
| 2015/0060696 A1 | 3/2015 | Dayton |
| 2015/0137762 A1 | 5/2015 | Kim et al. |
| 2017/0202988 A1 | 7/2017 | Clark |
| 2018/0008735 A1 | 1/2018 | Almeida |
| 2022/0151359 A1 | 5/2022 | Yang |

FOREIGN PATENT DOCUMENTS

| | | |
|---|---|---|
| KR | 10-2013-0005941 A | 1/2013 |
| KR | 10-1367256 B1 | 2/2014 |
| KR | 10-2014-0078873 A | 6/2014 |
| KR | 10-2017-0116832 A | 10/2017 |
| KR | 10-2018-0136258 A | 12/2018 |

SYSTEMS AND METHODS FOR SANITIZING MOBILE ELECTRONIC DEVICES

REFERENCE TO RELATED APPLICATIONS

This application is a continuation of U.S. patent application Ser. No. 17/444,255, filed Aug. 2, 2021, which claims the benefit of U.S. Provisional Application No. 63/125,942 filed Dec. 15, 2020, U.S. Provisional Application No. 63/090,054 filed Oct. 9, 2020, and U.S. Provisional Application No. 63/060,566 filed Aug. 3, 2020. This application hereby incorporates by reference the above-identified applications in their entireties.

BACKGROUND

Field

This disclosure relates generally to sanitizing devices and specifically to sanitizing mobile electronic devices.

Related Art

Mobile electronic devices (and other portable objects) are used by billions of people around the world. These devices are typically carried by a user in a pocket, purse, or backpack, and are continuously retrieved, viewed, and handled throughout the day. Microbes and other undesirable substances can accumulate on any such devices through contact with a user's hands or the environment, during storage, and in other contaminating events. For these reasons, a mobile electronic device (and other portable items) may act as a carrier for spreading microbes and causing infections.

SUMMARY

In some embodiments, this disclosure includes a description of a sanitizing system comprising a housing with an interior; an entry system with a default closed position, the entry system being configured to permit a mobile electronic device to pass through the entry system and then to automatically return to the default closed position; a sanitizer contained within the housing configured to emit radiation with a sanitizing effect; and a receiver system configured to receive a mobile electronic device (or item of similar shape) that is inserted into the housing, the receiver system configured to automatically move the mobile electronic device fully into the interior of the housing, to perform a sanitizing procedure on the mobile electronic device, and to automatically move the mobile electronic device at least partially outside of the housing, the receiver system comprising one or more holders comprising a film configured to help guide a mobile electronic device into and out of the sanitizing system.

In some embodiments, this disclosure also includes a description of a sanitizing system for sanitizing a mobile electronic device comprising: a housing; a sanitizer contained within the housing configured to emit radiation with a sanitizing effect; and an entry system with a default closed position, the entry system being configured to permit a mobile electronic device to pass through the entry system and then automatically return to the default closed position, the entry system comprising a first outer enclosure and a second inner obstruction; wherein the entry system blocks radiation emitted within the sanitizing system to a level acceptable for consumer use, wherein the second inner obstruction provides more radiation attenuation than the first outer enclosure, and/or wherein the combination of the first outer enclosure and the second inner obstruction provides more radiation attenuation than the first outer enclosure by itself.

BRIEF DESCRIPTION OF THE DRAWINGS

Some of these drawings are schematic, showing some examples of basic parts and concepts. Many different or additional structures, implementations, components, mechanisms, steps, and processes can be used. The claimed inventions should not be limited in any way to anything illustrated in the drawings.

DETAILED DESCRIPTION

Figure 1A:
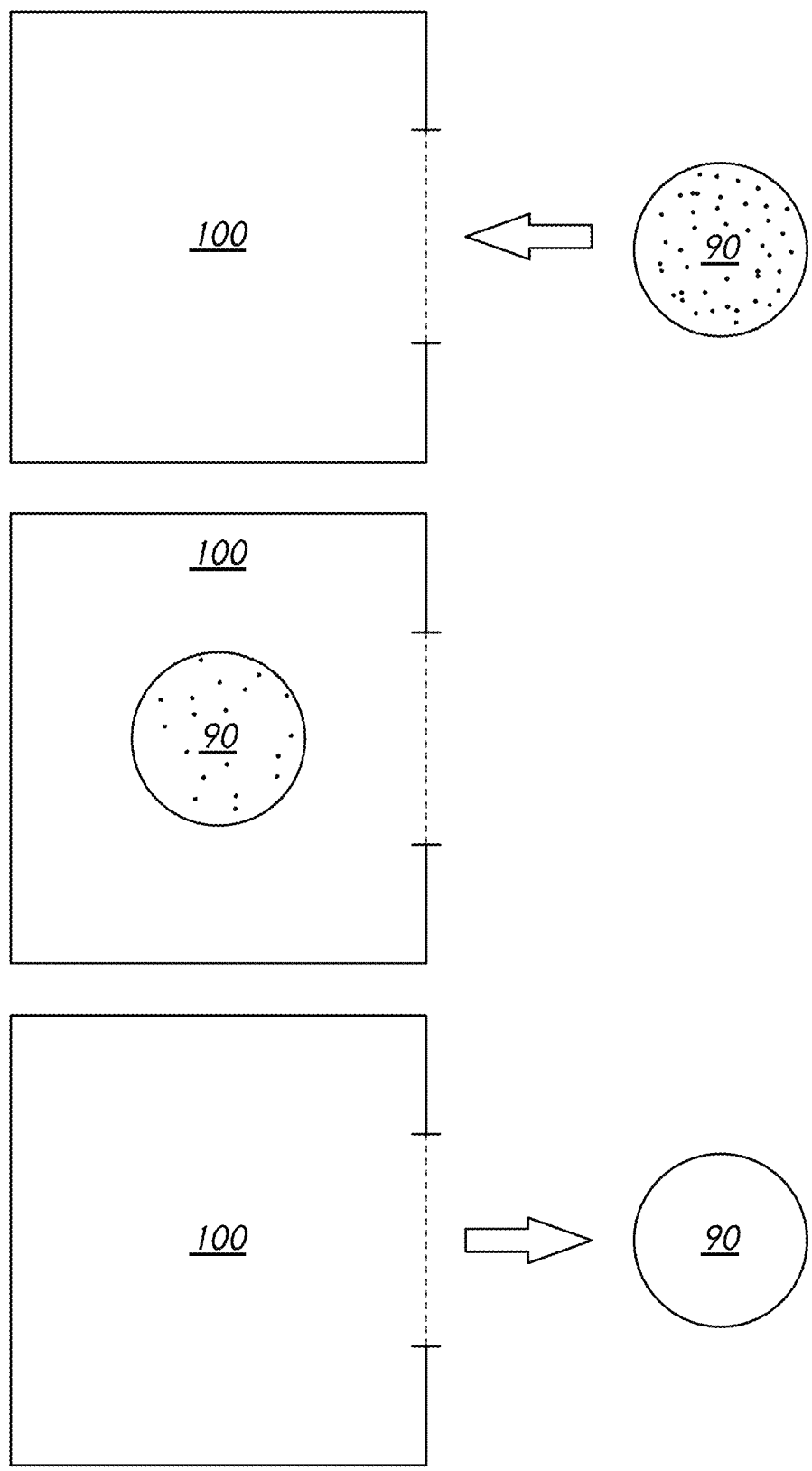
FIG. 1A is a schematic illustration of a sanitizing system in three stages of use and an object that is sanitized.

This specification provides textual descriptions and illustrations of many devices, components, assemblies, and subassemblies. Any structure, material, function, method, or step that is described and/or illustrated in one example can be used by itself or with or instead of any structure, material, function, method or step that is described and/or illustrated in another example or used in this field. The text and drawings merely provide examples and should not be interpreted as limiting or exclusive. No feature disclosed in this application is considered critical or indispensable. The relative sizes and proportions of the components illustrated in the drawings form part of the supporting disclosure of this specification, but should not be considered to limit any claim unless recited in such claim.

As illustrated in FIG. 1A, a sanitizing system 100 can be configured to removably receive an object 90 for sanitizing. The object 90 can be inserted by a user at least partially through an opening in the sanitizing system 100 or placed on, near, or at least partially or entirely within the sanitizing system 100. The sanitizing system 100 receives the object 90 within the interior of the sanitizing system 100, performs a sanitizing operation on the object 90, and then at least partially ejects the object 90 or makes the object 90 available for removal by the user in a sanitized state. In some embodiments, the sanitizing system 100 can perform the sanitizing operation using electromagnetic radiation and/or in some other way, such as by heating, chemical disinfectant, washing (e.g., spraying with and/or immersing in water and/or soap), and/or physical contact such as wiping or scrubbing. All embodiments disclosed in this specification illustrate and/or describe features that can be used with the sanitizing system 100 illustrated in FIG. 1A. It is contemplated that any combination of features from any embodiment or multiple embodiments in this specification can be used in or with the sanitizing system 100 illustrated in FIG. 1A.

Figure 1B:
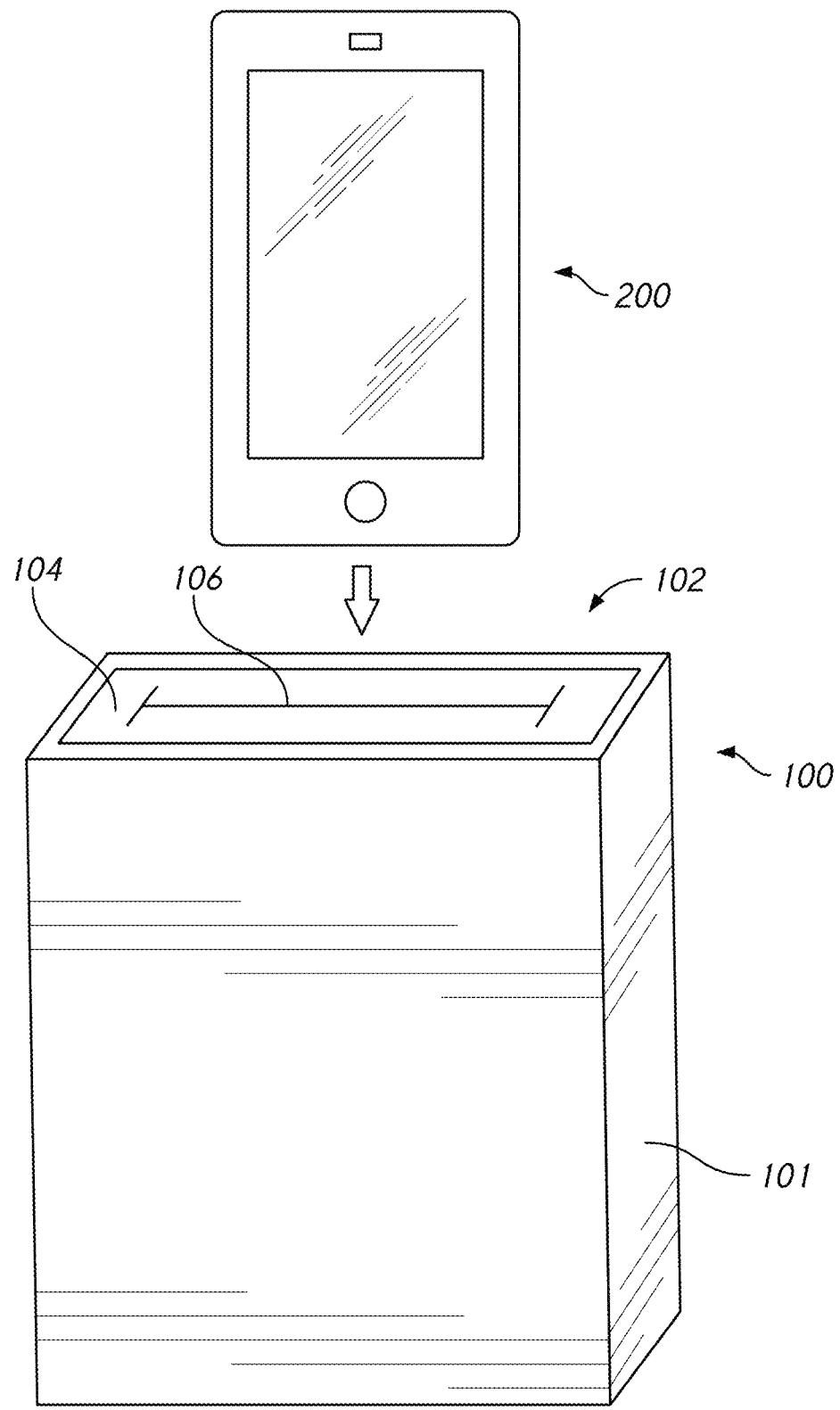
FIG. 1B is an illustration of a front perspective view of an example of a sanitizing system of FIG. 1A and a mobile electronic device that is about to be inserted into the sanitizing system.

In some embodiments, as illustrated in FIG. 1B, a mobile electronic device 200 is the object 90 to be sanitized. Any type of mobile electronic device 200 can be used, such as one or more of mobile telephones, mobile audio devices (e.g., wired or wireless earphones and/or microphones), mobile gaming devices, mobile electronic storage devices (e.g., configured to store music, photos, or other data), mobile cameras, mobile GPS devices, mobile inventory devices, mobile compact computers (e.g., computer tablets or laptops), mobile access actuators (e.g., electronic keys, or door or gate openers), mobile chargers, remote controls, mobile product scanners, mobile ticket-scanning devices, and/or mobile identification devices, etc.

In some embodiments, the sanitizing system 100 can also or alternatively be adapted to be used with any other products that commonly encounter microbes and can benefit from being sanitized, including one or more other products that are commonly handled by human hands, such as keys or key sets, ID badges, grooming and hygiene products (hair combs and brushes, tooth brushes, etc.), financial cards (e.g., credit or debit cards), face or respiration masks, writing implements (e.g., pens, pencils, touch-screen stylets, etc.), jewelry (e.g., rings, bracelets, necklaces, etc.), coins or tokens, gloves, eating utensils, tools, medical instruments or devices, keyboards, etc. Any place in this specification that refers to mobile electronic devices is intended to also disclose and contemplate the use and sanitizing of any of such types of devices that are commonly handled by or in contact with human hands.

Figure 2:
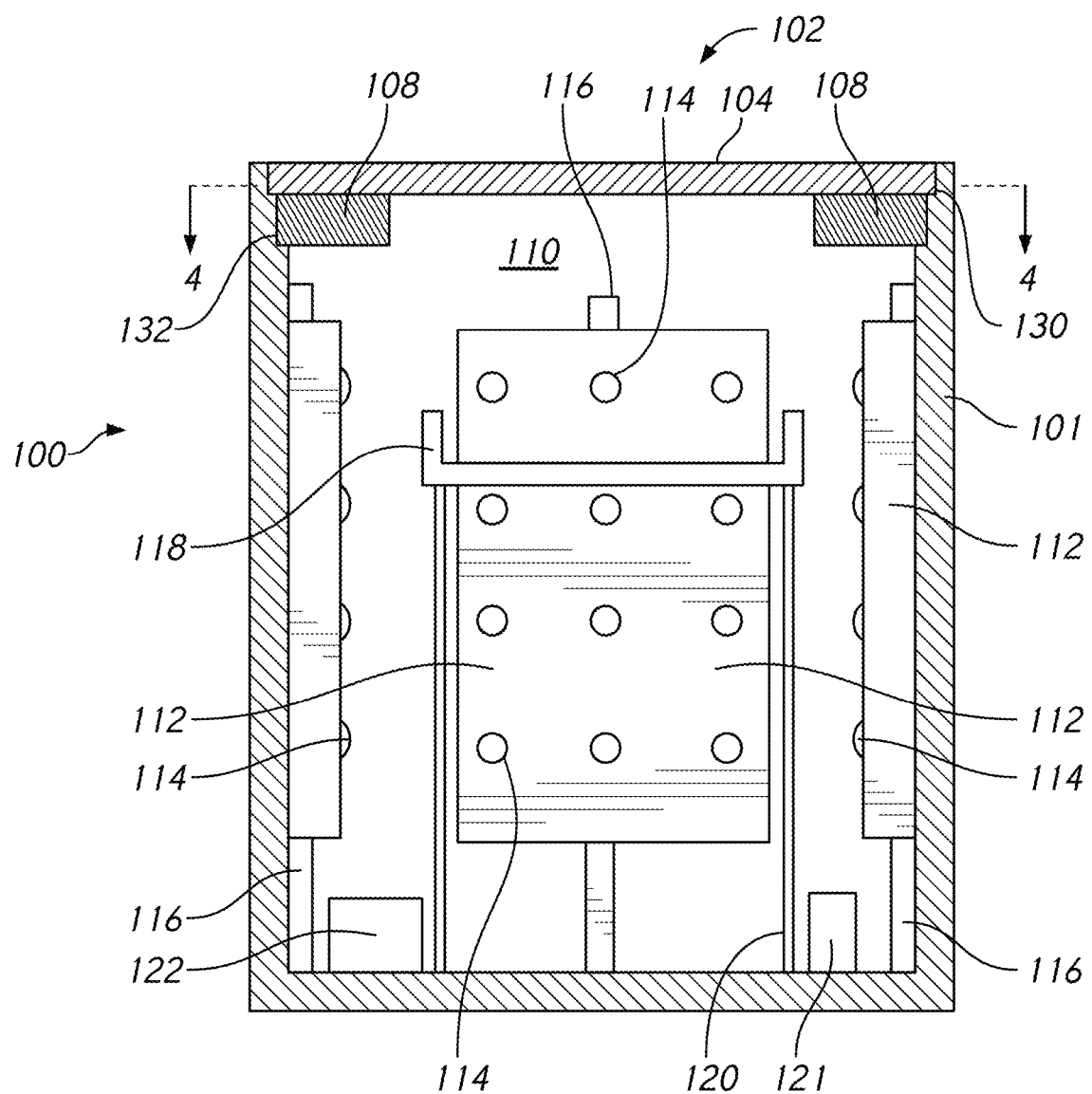
FIG. 2 is a schematic illustration of a vertical cross-sectional view of the sanitizing system of FIG. 1B.

As shown in FIG. 1B, the sanitizing system 100 can include a housing 101 with an entry system 102 comprising a first outer enclosure 104 with a closeable opening. In the illustrated example, the closeable opening is formed as an elongate slit 106. As shown in FIG. 2, the entry system 102 can include a second inner obstruction 108, which in some embodiments as shown can comprising a plurality of separate lateral portions (e.g., a left lateral portion and a right lateral portion). The second inner obstruction 108 can be separate from the first outer enclosure 104. The second inner obstruction 108 can be made of a different material than the first outer enclosure 104. For example, the second inner obstruction 108 can be more opaque to one or more types of radiation, such as one or more types of UV radiation. The second inner obstruction 108 can have a different shape or size than the first outer enclosure. For example, the second inner obstruction 108 can be thicker than the first outer enclosure 104 (e.g., larger in the vertical dimension as shown). In some embodiments, the second inner obstruction 108 can be formed, structured, and/or configured to move independently or separately from the first outer enclosure 104 in some or all circumstances (see, e.g., FIG. 7). As illustrated, in some embodiments, the first outer enclosure 104 and the second inner obstruction 108 can be adjacent to and in contact with each other such that the movement of the first outer enclosure 104 can induce movement of the second inner obstruction 108 in some or all circumstances (see, e.g., FIG. 5).

The first outer enclosure 104 can be made of any suitable material, such as an elastomeric, flexible, or resilient material (e.g., silicone or rubber). The first outer enclosure 104 can be sized to fit within a proximal opening in the housing 101, which can be formed with a ledge or inset surface to provide a first distal support 130 within the housing 101 for the first outer enclosure 104. The first outer enclosure can be configured to close the proximal opening in the housing 101.

The second inner obstruction 108 can be sized to fit within a region of the housing 101 distal from the first distal support 130, which can be formed with a ledge or inset surface to provide a second distal support 132 within the housing 101 for the second inner obstruction 108. The second inner obstruction 108 can be made of any suitable material, such as a material that is helpful in impeding or blocking radiation (e.g., UV rays). For example, the second inner obstruction 108 can be made of an opaque material, a flexible material (e.g., silicone) infused with carbon black, a material with a metallic coating or layer on its underside, and/or a polymer such as polycarbonate. Either or both of the first outer enclosure 104 and the second inner obstruction 108 can be attached and/or secured to the housing 101 or to the sanitizing system 100 generally in any suitable way, such as by friction fit, interference fit, stretching attachment, adhesive, solvent, sonic welding, and/or one or more hinges of any type, etc. In some embodiments, the second inner obstruction 108 provides more radiation attenuation than the first outer enclosure 104, and/or the combination of the first outer enclosure 104 and the second inner obstruction 108 provides more radiation attenuation than the first outer enclosure by itself 104, such that the sanitizing system 100 does not leak out radiation in a clinically significant amount to avoid harm to persons who routinely use the sanitizing system 100.

The sanitizing system 100 can comprise a sanitizer that includes one or more devices and methods for sanitizing items such as mobile electronic devices 200 that are inserted into an interior chamber 110 of the housing 101. The sanitizer can comprise one or a plurality of sanitizing panels 112, each of which can comprise one or a plurality of sanitizing or radiation-emitting sources 114, such as LED lights. For example, as shown, panels 112 of one or more sanitizing sources 114 can be provided on any or all of lateral sides, on a rear side, and on a front side (not shown). In some embodiments, the sanitizing sources 114 can emit radiation with wavelengths that include or encompasses some portion or all of the UV range, such as greater than or equal to about 100 nm and/or less than or equal to about 400 nm. In some embodiments, the sanitizing sources can emit radiation with wavelengths that include or encompass some portion or all of the UV-A range, such as greater than or equal to about 315 nm and/or less than or equal to about 400 nm; the UV-B range, such as greater than or equal to about 280-315 nm and/or less than or equal to about 280 nm; and/or the UV-C range, such as greater than or equal to about 100 nm and/or less than or equal to about 280 nm.

As illustrated in FIG. 2, the sanitizing sources can be attached to or mounted on one or more of the sanitizing panels 112, which can be movable, such as up and down in a vertical direction on a mover 116, such as a rail, cable, solenoid, or any other suitable electrical or motorized system for inducing controlled movement.

The sanitizing system 100 can include a receiver 118 that is configured to receive and/or securely grasp the mobile electronic device 200 and to automatically convey the mobile electronic device 200, when manually inserted at least partially into the sanitizing system 100, further into and/or out of the interior chamber 110 of the housing 101. The receiver 118 can be movable by any suitable conveyor 120 system such as a rail, cable, screw, solenoid, and/or any other suitable electrical or motorized system for inducing controlled movement. The sanitizing system 100 can include one or more sensors (e.g., optical sensors, proximity sensors, pressure sensors, movement sensors, etc.) to automatically detect when the mobile electronic device has been inserted at least partially into the sanitizing system 100. The one or more sensors can be in electrical communication with an electronic processor 121 in the sanitizing system 100 that, in response to the detection of the mobile electronic device 200, can actuate the receiving system to move the mobile electronic device 200 further into the interior of the sanitizing system 100. In some embodiments, the user only places the mobile electronic device 200 on or near the housing 101 of the sanitizing system 100, or the user only inserts the mobile electronic device 200 partially into the housing 101 of the sanitizing system 100 as shown, and then the receiver system moves the mobile electronic device 200 the rest of the way fully into the sanitizing system 100 such that the mobile electronic device 200 is enclosed or enveloped within the housing 101 of the sanitizing system 100. In some embodiments, one or more sensors (e.g., of the type disclosed herein) is or are configured to detect any jam, irregular or improper movement of the mobile electronic device 200, and/or any other situation where electromagnetic radiation could otherwise be emitted outside of the sanitizing system 100, such that in response the electronic processor 121 in communication with such one or more sensors can be configured to halt or not initiate a sanitizing procedure as a safety precaution to avoid escape of electromagnetic radiation.

Either, some, or all of the mover 116 of the sanitizing panels 112, the conveyor of the receiver 118, and/or the sanitizing sources 114 can be in electronic communication with and/or controlled by the electronic processor 121. The sanitizing system 100 can receive electrical power from a power source 122, such as a portable electrical power source (e.g., a rechargeable battery) or a fixed-location electrical power source (e.g., an electrical wire configured to be attached to an electrical outlet).

Figure 3:
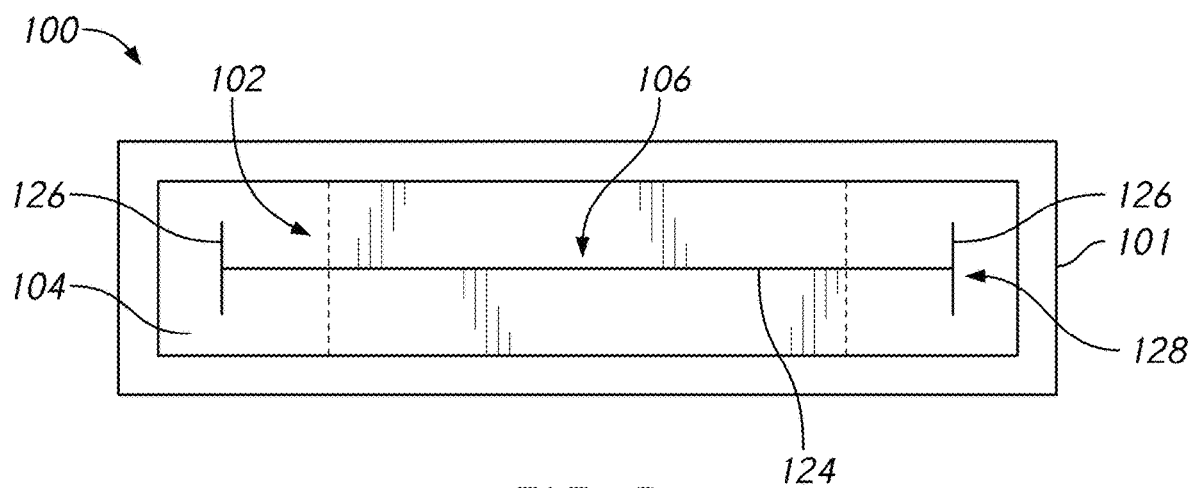
FIG. 3 is an illustration of a top view of the sanitizing system of FIG. 1B.
Figure 4A:
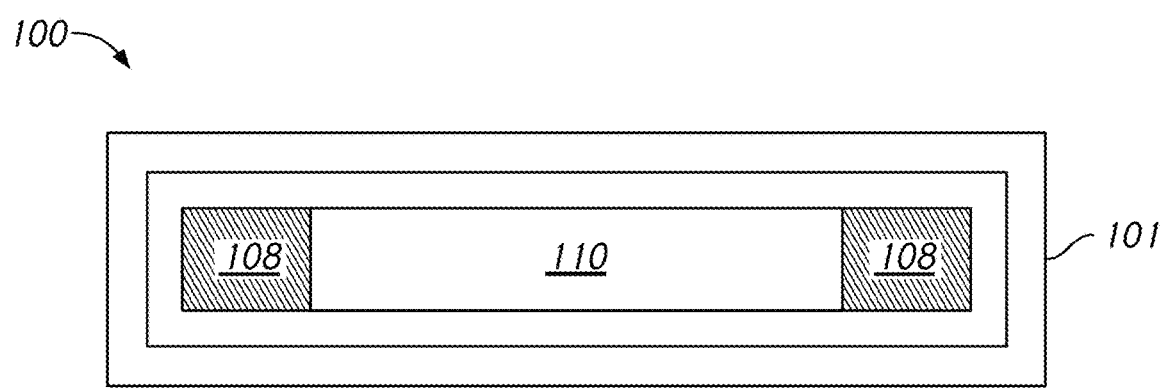
FIG. 4a is an illustration of a horizontal cross-sectional view of the sanitizing system of FIG. 2, taken along the line 4-4.

As shown in FIGS. 3 and 4a, the closeable opening or elongate slit 106 of the first outer enclosure 104 of the entry system 102 can comprise a transverse portion 124 that is generally perpendicular to the vertical height of the sanitizing system 100, and the elongate slit 106 can comprise one or a plurality of abutting portions 126 that are generally perpendicular to the transverse portion 124. In the illustrated example, the elongate slit 106 can provide increased opening space and lower likelihood of tearing and greater versatility in opening width to accommodate or receive mobile electronic devices 200 of different widths. In some embodiments, the sanitizing system 100 is sufficiently large, both in width and height, to fully receive the majority of mobile phones on the market, including those housed within the majority of cases on the market. However, the joining points 128 at which the transverse portion 124 contact or intersect the abutting portions 126 may provide a region of greater risk or possibility that radiation emitted from within the housing 101 could pass outside of the housing 101. As shown in FIG. 4a, the second inner obstruction 108, positioned below the first outer enclosure 104 and within the interior chamber 110 of the housing 101, can serve to obstruct, resist the passage of, or substantially or entirely block radiation generated from within the housing 101 from passing through the region encompassing or within or near the joining points 128, thereby blocking radiation leakage or ensuring that any radiation that leaks out through the entry system 102 is at a level acceptable for consumer exposure over a prolonged and repeated period of use.

Figure 4B:
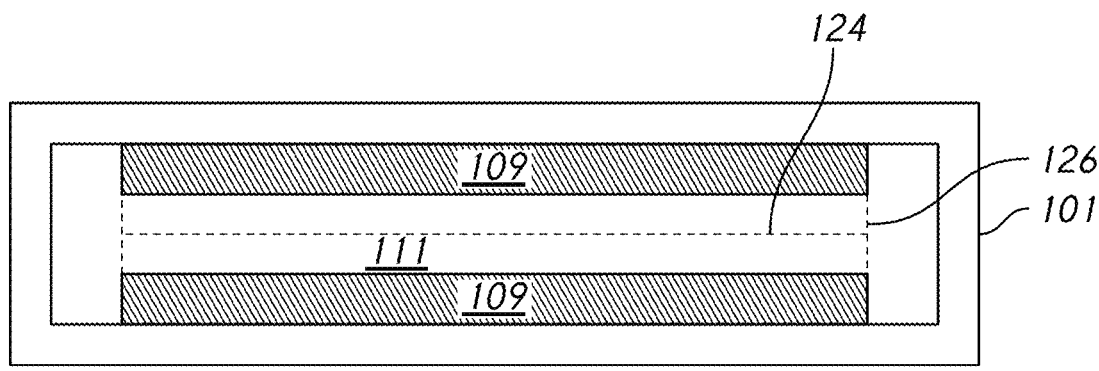
FIG. 4b is a view similar to that of FIG. 4a, showing a different shape and position for an inner obstruction.

FIG. 4b shows different inner obstructions 109. These are generally aligned with and positioned on either side or both sides of the transverse portion 124 of the elongate slit 106. These inner obstructions 109 can serve to support a material of an outer enclosure 104 to reduce or delay cracking or other harmful consequences of repeated use. They can reduce a tendency for an outer enclosure 104 to crease, curl, gape, rip, or pucker, for example. They can also resiliently assist in positioning and centering a device 200 as it is inserted into an entry system 102. The obstructions 109 can be formed from a resilient, long-lasting, UV-resistant material. The obstructions 109 can be strips of foam and can help in protecting/buffering a flexible cover (e.g., an outer enclosure 104) from stress and strains. They can help prevent the cover from deforming and ripping upon insertion of an object to be sanitized (especially over many cycles). The obstructions 109 can be adhered smoothly to a lower surface of an outer enclosure 104. The obstructions 109 can extend along or across all or a majority of the distance of the top of the sanitizing system 100 from one lateral side to the opposite later side and/or the obstructions 109 can extend along or across all or a majority of the distance of the slit 106. They can be supported by and rest on more rigid hinged structures that allow them to open and swing inward and downward. The properties, benefits and functions described with respect to the obstructions 109 can also apply to the obstructions 108, and vice-versa.

Figure 4C:
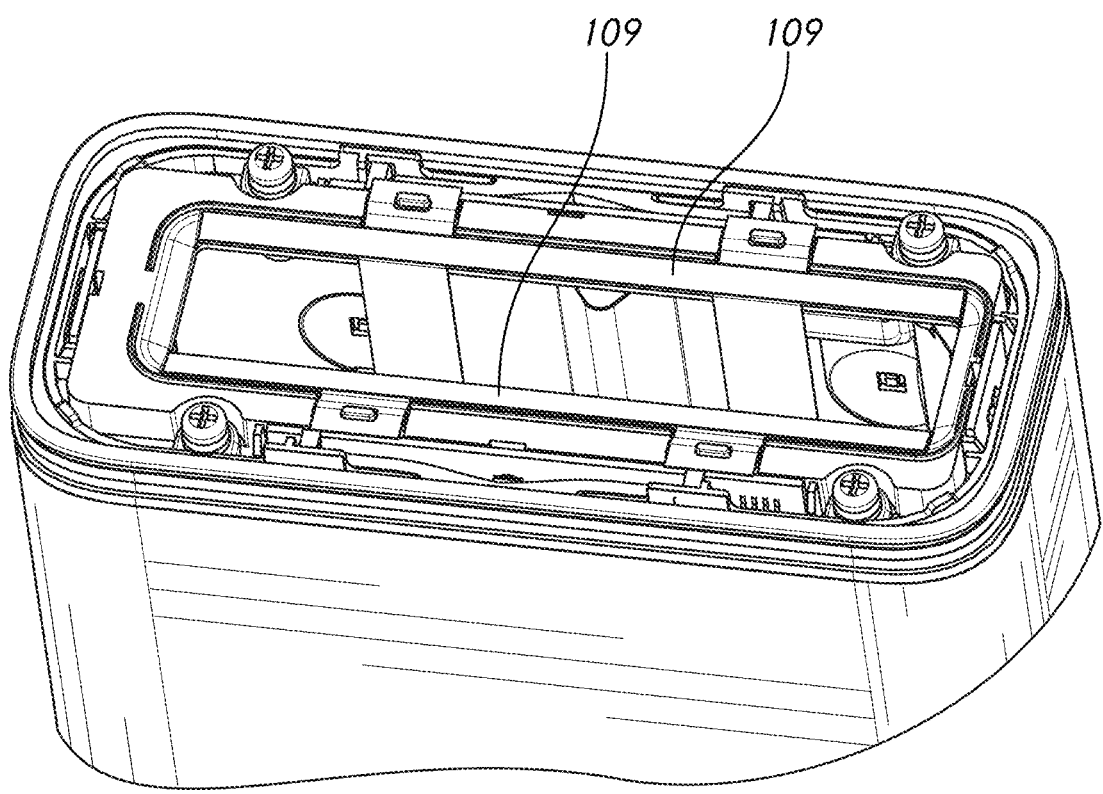
FIG. 4c is a partial perspective view showing an implementation of the inner obstruction schematically shown in FIG. 4b.

FIG. 4c shows how an inner obstruction 109 can be implemented. An outer enclosure 104 has been removed for illustration purposes in this figure to reveal underlying structures. In some embodiments, a sanitizing system can have an inner obstruction comprising two strips of resilient material thicker than the outer enclosure and positioned immediately adjacent to and/or in contact with either side or both sides of an opening in, and configured to support, the outer enclosure and thereby inhibit wear and deterioration of the outer enclosure.

Figure 5:
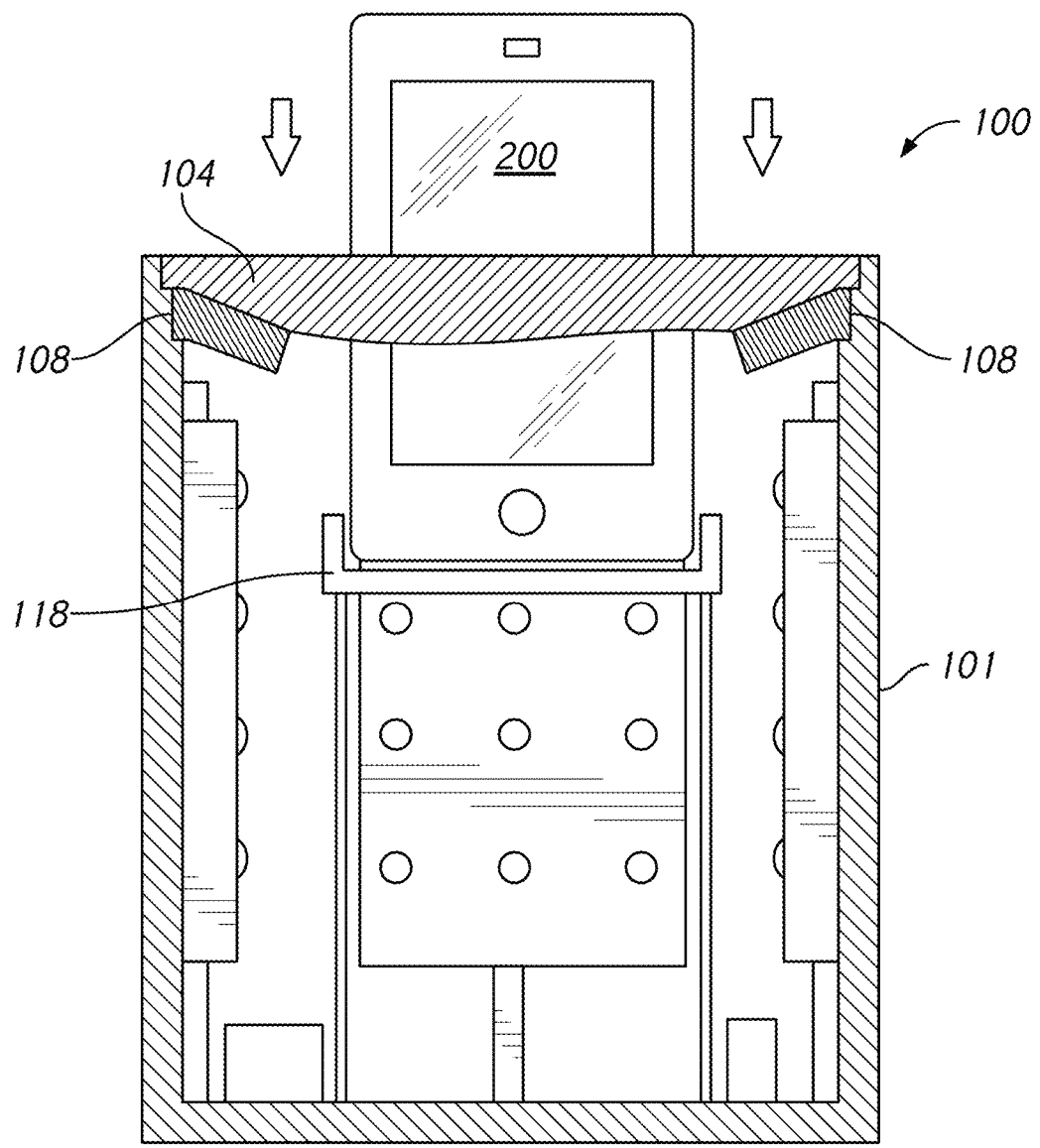
FIG. 5 is a schematic illustration of a vertical cross-sectional view of the sanitizing system of FIG. 1B with the mobile electronic device partially inserted into the sanitizing system.

FIG. 5 shows that when the mobile electronic device 200 is manually partially inserted into the entry system 102 of the sanitizing system 100 (e.g., by passing through the elongate slit 106 of the first outer enclosure 104) and then engages with, contacts, latches onto, is received into, and/or otherwise encounters the receiver 118, the mobile electronic device 200 is automatically conveyed by the receiver 118 fully into the interior chamber 110 of the housing 201. When the top of the mobile electronic device 200 passes distally beyond the entry system 102, such that the mobile electronic device 200 is positioned entirely within the housing 101, the entry system 102 returns to its default closed position. In some embodiments, as illustrated, at least a portion of the entry system 102 (e.g., the first outer enclosure 104), is configured to deform, stretch, expand, or otherwise move to snuggly or tightly or closely permit the mobile electronic device 200 to enter the housing 101 while resisting the creation of large or significant openings or spaces surrounding the mobile electronic device 200 during insertion. In some embodiments, the first outer enclosure 104 contacts or forms a loose or tight seal around the periphery of the mobile electronic device 200 during insertion. As illustrated, as the first outer enclosure temporarily moves distally into the interior chamber 110, the second inner obstruction can also flex, deflect, tilt, turn, bend, hingedly rotate, or otherwise move further distally into the interior chamber 110 of the housing 101.

Figure 6:
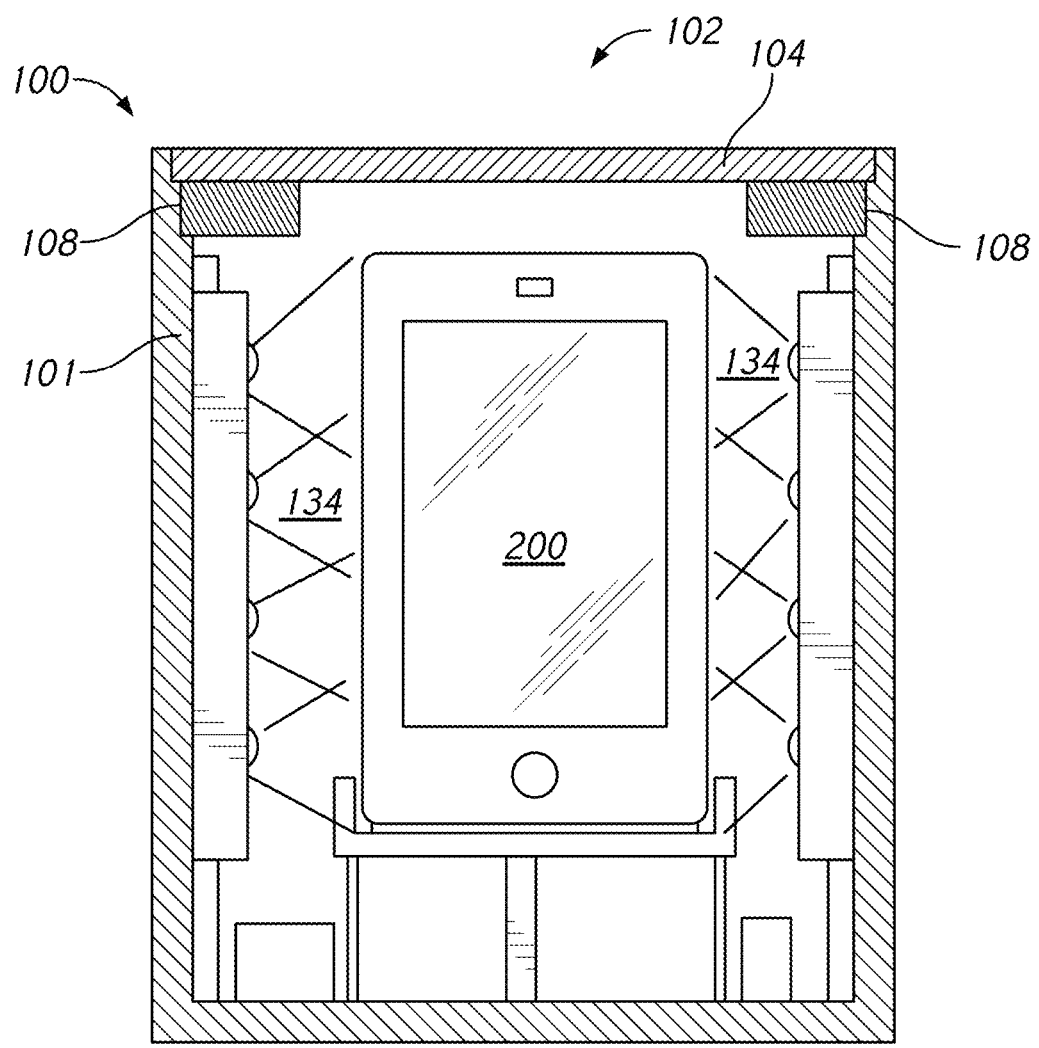
FIG. 6 is a schematic illustration of a vertical cross-sectional view of the sanitizing system of FIG. 1B with the mobile electronic device fully inserted into the sanitizing system with sanitizing radiation being emitted onto the mobile electronic device.

As illustrated in FIG. 6, when the mobile electronic device 200 is received into the housing 101 of the sanitizing system, the entry system 102 can automatically and immediately return to its default closed position, and the second inner obstruction 108 can automatically and immediately return to its default position adjacent to, in contact with, near, and/or distal from the first outer enclosure 104. If the first outer enclosure 104 includes an elongate slit 106 with joining points 128 (as illustrated in FIGS. 1 and 3), then the second inner obstruction 108 can be positioned between the one or plurality of sanitizing sources 114 in an impeding, shielding, and/or blocking matter to enable the second inner obstruction 108 to resist the leakage of radiation outside of the housing 101 of the sanitizing system 100 especially at the joining points 128.

As shown, radiation 134 can be emitted from one of more of the sanitizing sources 114 such that the radiation 134 impinges upon and sanitizes one or more or all sides of the inserted mobile electronic device 200. The processor can be configured to control the sanitizing system 100 such that radiation 134 can be emitted at any suitable wavelength (including but not limited to those UV wavelengths described elsewhere in this specification) and for any suitable duration sufficient to kill microbes that commonly accumulate on mobile electronic devices 200 during normal use and/or that present any significant clinical risks to human health. In some embodiments, the duration and/or wavelength or any other feature or property of the sanitizing system or process can be adjusted, either directly or indirectly, by a user selection received by the processor through any suitable user-input device, such as a screen and keypad or a touch screen or a wireless connection with a mobile electronic device 200. The sanitizing system 100 can include an audio system to provide information to the user by way of one or more sounds to indicate when the sanitation process is occurring and/or when it is or will be completed. In some embodiments, one or more or both of the radiation sources 114 and/or the mobile electronic device 200 can be moved during irradiation to help provide generally even coverage of radiation across all surfaces of the mobile electronic device 200 or at least on all surfaces of the mobile electronic device 200 that are likely to be contaminated during daily use.

Some embodiments can accomplish sanitizing of the mobile electronic device 200 without the use of any liquid such as soap, water, and/or alcohol, which could otherwise damage one or more liquid-sensitive electronic components of the mobile electronic device 200. Some embodiments, as shown, include a housing 101 that is not hinged or foldable or articulable on a side and/or does not expose the interior chamber 110 of the housing during insertion and/or removal of the mobile electronic device 200. In some embodiments, as shown, the opening in the housing 101 that is configured to receive the mobile electronic device 200 is positioned only on and/or extends only along one side of the housing 101, and there is no opening or portion of an opening configured to receive the mobile electronic device 200 and/or to open the housing 101 that is also positioned on and/or also extends along another side of the housing 101. In some embodiments, as shown, there is no openable seam, no openable part line, and/or no openable gap, along multiple sides of the housing 101 that is configured to provide an entry into the housing 101 through which the mobile electronic device 200 can be inserted or by which the housing 101 can be opened or that can facilitate placing of the mobile electronic device 200 into an interior space of the housing 101. In some embodiments, as shown, the mobile electronic device 200 can be inserted into and retrieved from the housing 101 entirely without requiring a user to touch any part of the sanitizing system 100 with the user's hands. For example, as shown, the user can grasp the mobile electronic device 200 while inserting it into the sanitizing system 100 and later the user can grasp the mobile electronic device 200 to remove it from the sanitizing system 100 after a sanitizing procedure has been performed, without directly touching and/or directly actuating a lid, door, hatch, opening, button, external sensor, and/or any other part of the inside and/or outside surface(s) of the sanitizing system 100, during either the insertion and/or removal of the mobile electronic device 200 into and/or from the sanitizing system 100. When a user is not required to touch the sanitizing system 100 to insert or withdraw the mobile electronic device 200, the risk of transmitting microbes by way of intermediate contact with the housing 101 of the sanitizing system 100 is diminished or eliminated. In some embodiments, the mobile electronic device 200 can be sanitized completely on all sides in a single cycle, without requiring a user to turn, flip, or otherwise move or reposition the mobile electronic device 200 before performing another cycle or phase of a sanitizing procedure.

Figure 7:
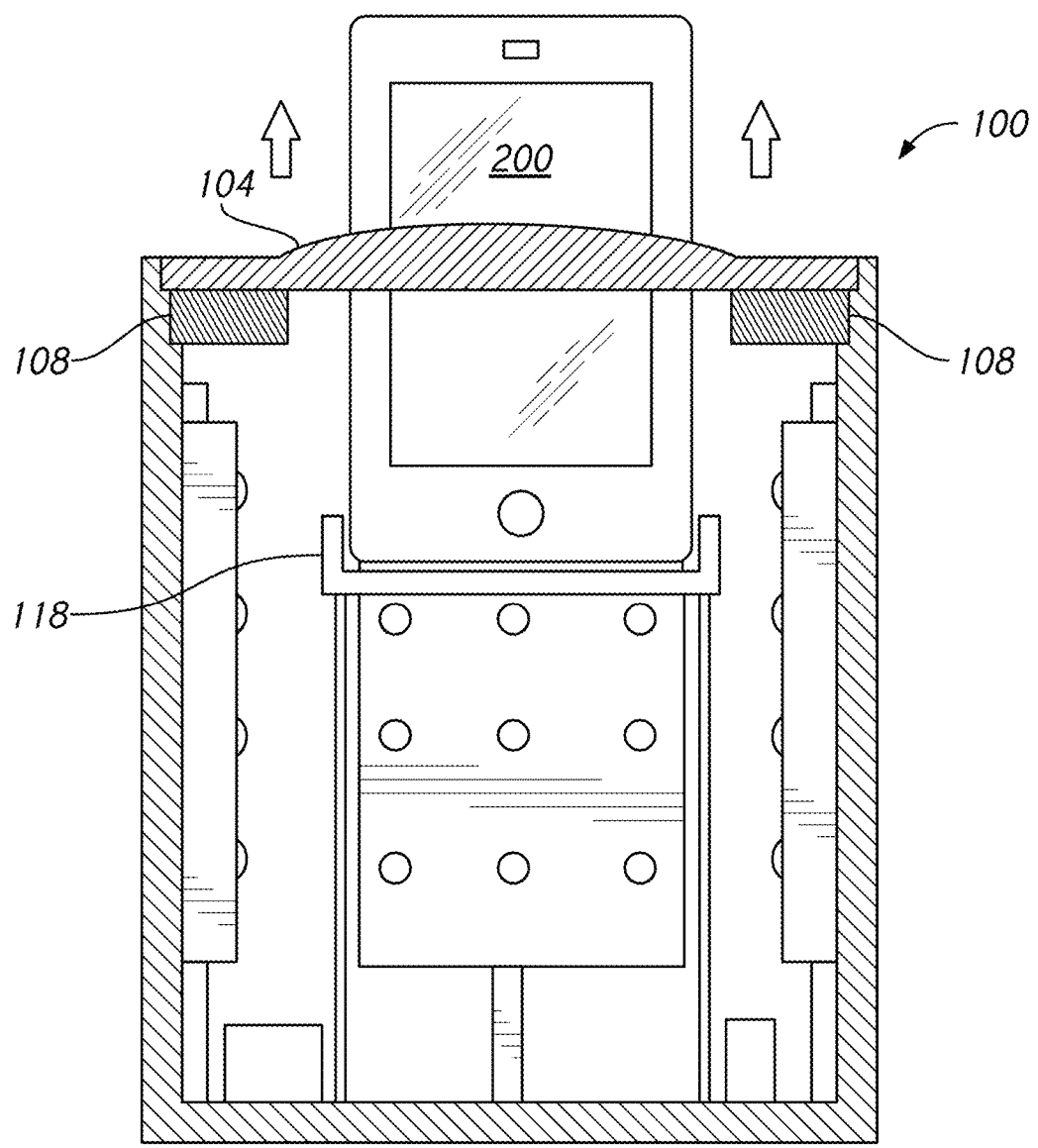
FIG. 7 is a schematic illustration of a vertical cross-sectional view of the sanitizing system of FIG. 1B as the mobile electronic device is partially ejected from the sanitizing system.

FIG. 7 demonstrates that when the sanitizing process is complete and the sanitizing sources 114 are no longer emitting radiation, the receiver 118 can advance the mobile electronic device 200 in an upward or proximal direction such that at least part of the mobile electronic device 200 passes through the entry system 102, forcing it to open temporarily, such that the mobile electronic device 200 can temporarily protrude upwardly or proximally above the sanitizing system 100 in a position to be grasped by a user. In some embodiments, the irradiation of the mobile electronic device 200 continues as the mobile electronic device 200 is advanced proximally or upwardly outside of the sanitizing system 100. During this phase, the first outer enclosure 104 can temporarily stretch, deform, elongate, or otherwise move upwardly, forming relatively tight or generally close contact and/or a seal around the mobile electronic device 200. In some embodiments, as shown, during upward or proximal advancement of the mobile electronic device 200 and/or when the mobile electronic device 200 is protruding through the entry system 102, the second inner obstruction 108 does not flex, deflect, tilt, turn, bend, hingedly rotate, or otherwise move in any appreciable amount.

All embodiments disclosed in this specification can include or can be used with or instead of any structure, material, function, method, or step that is described and/or illustrated in connection with the embodiments of FIGS. 1-7 of this specification.

Figure 8:
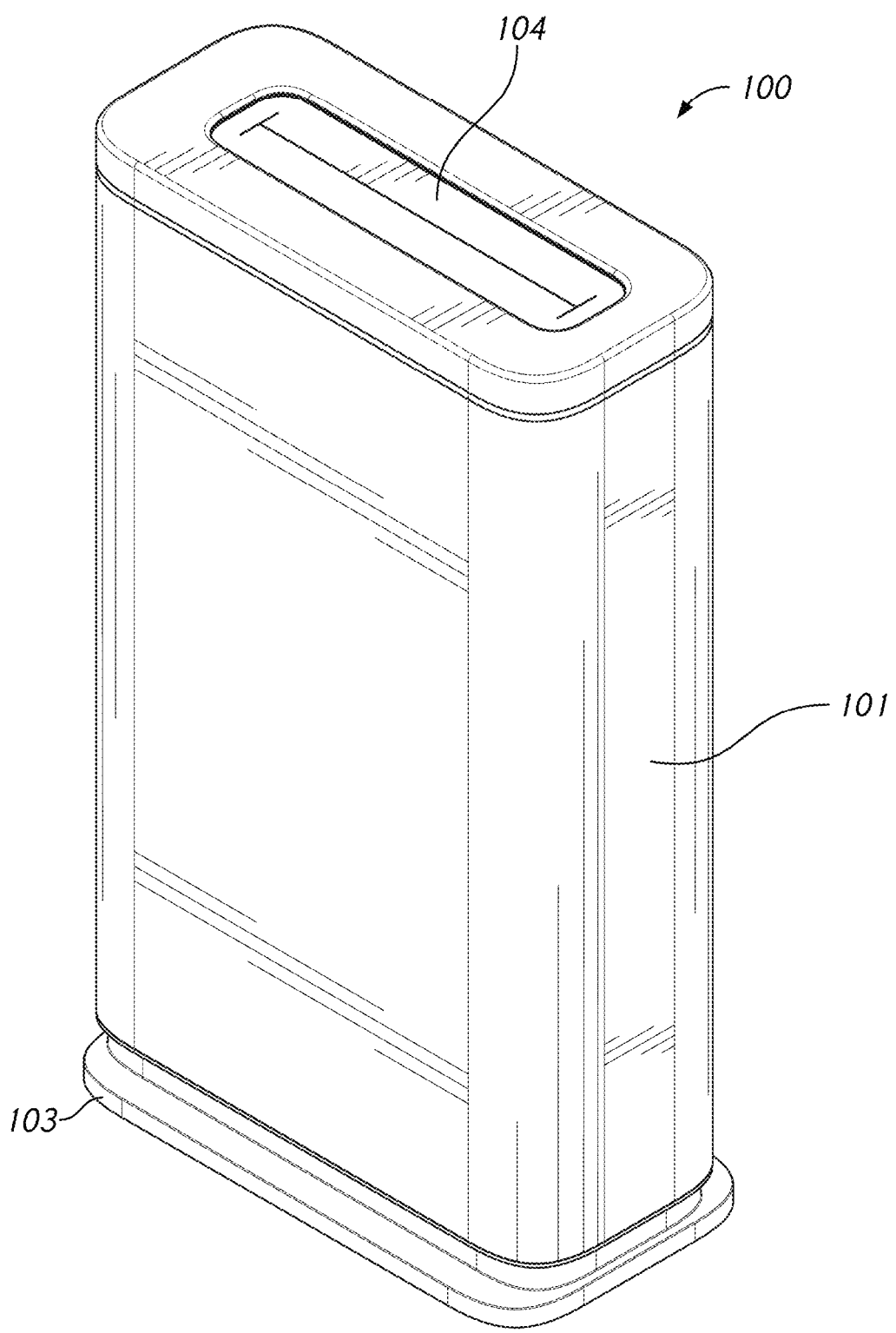
FIG. 8 is a front perspective view of another example of a sanitizing system of FIG. 1A.

Another example of a sanitizing system 100 is illustrated in FIGS. 8-13. As shown in FIG. 8, the housing 101 can comprise a height measurement that is substantially larger than its width or depth measurements. In some embodiments, the dimensions of the housing 101 (e.g., width, depth, and/or height) can each be no more than about 20% larger or no more than about 50% larger than each of the dimensions of the types of mobile electronic devices that are intended to be sanitized by the sanitizing system 100.

The housing 101 can comprise a base 103 positioned at the bottom of the housing. As shown, the base 103 can comprise a width and/or depth that is larger than the width and/or depth of the portion of the housing above the base 103 to provide increased stability by resisting tipping or wobbling as a mobile electronic device is inserted into or withdrawn from the sanitizing system 100. The enclosure 104 can be located in a non-flush recessed position with respect to an upper portion of the housing 101. In some embodiments, any housing 101 in this specification can be formed at least in part of a generally rigid material, such as a metal (e.g., stainless steel) or a polymer (e.g., plastic) or any combination of metal and polymer portions, or any other suitable material.

In the embodiment shown in FIG. 8, the housing 101 of the sanitizing system 100 comprises an enclosure with six sides: a top, a bottom, a left side, a right side, a front side, and a rear side. As shown, the opening to receive and eject the mobile electronic device 200 is provided on only a single side. The opening can be provided on any single side or can span multiple sides. In some embodiments in which the opening is provided on only a single side, the interior of the sanitizing system 100 can be maintained in a more sanitary, debris-free, and otherwise protected condition than when the entire interior of the housing is exposed when opening up and inserting or retrieving the mobile electronic device 200 from within the sanitizing system 100, such as in a hinged clam-shell type housing arrangement where a user's fingers are likely to touch the interior of the sanitizing system 100. In some embodiments, as shown, the interior of the housing 101 of the sanitizing system 100 cannot be touched by a user during normal use (and without partial or complete disassembly or removal of one or more components of the housing 101) and/or one or more structures or configurations of the sanitizing system 100 can resist contact between the interior of the housing 101 of the sanitizing system 100 and the user and/or the user's fingers in normal use. In the illustrated embodiments, the housing 101 can remain generally or substantially closed even when the mobile electronic device 200 is inserted or ejected from the housing 101, by virtue of the single-side opening and the closeable opening with the outer enclosure 104. In some embodiments, as shown, the user's experience with the device is made easier by permitting the user to simply activate the sanitizing system 100 by pushing a mobile electronic device 200 into the single-side opening and retrieving the mobile electronic device 200 from the same single-side opening when the sanitizing process is complete and the mobile electronic device 200 is ejected, without requiring the user to manually open the housing 101, precisely position the mobile electronic device 200 within the cavity of the housing 101, and/or manually close the housing 101.

Figure 9:
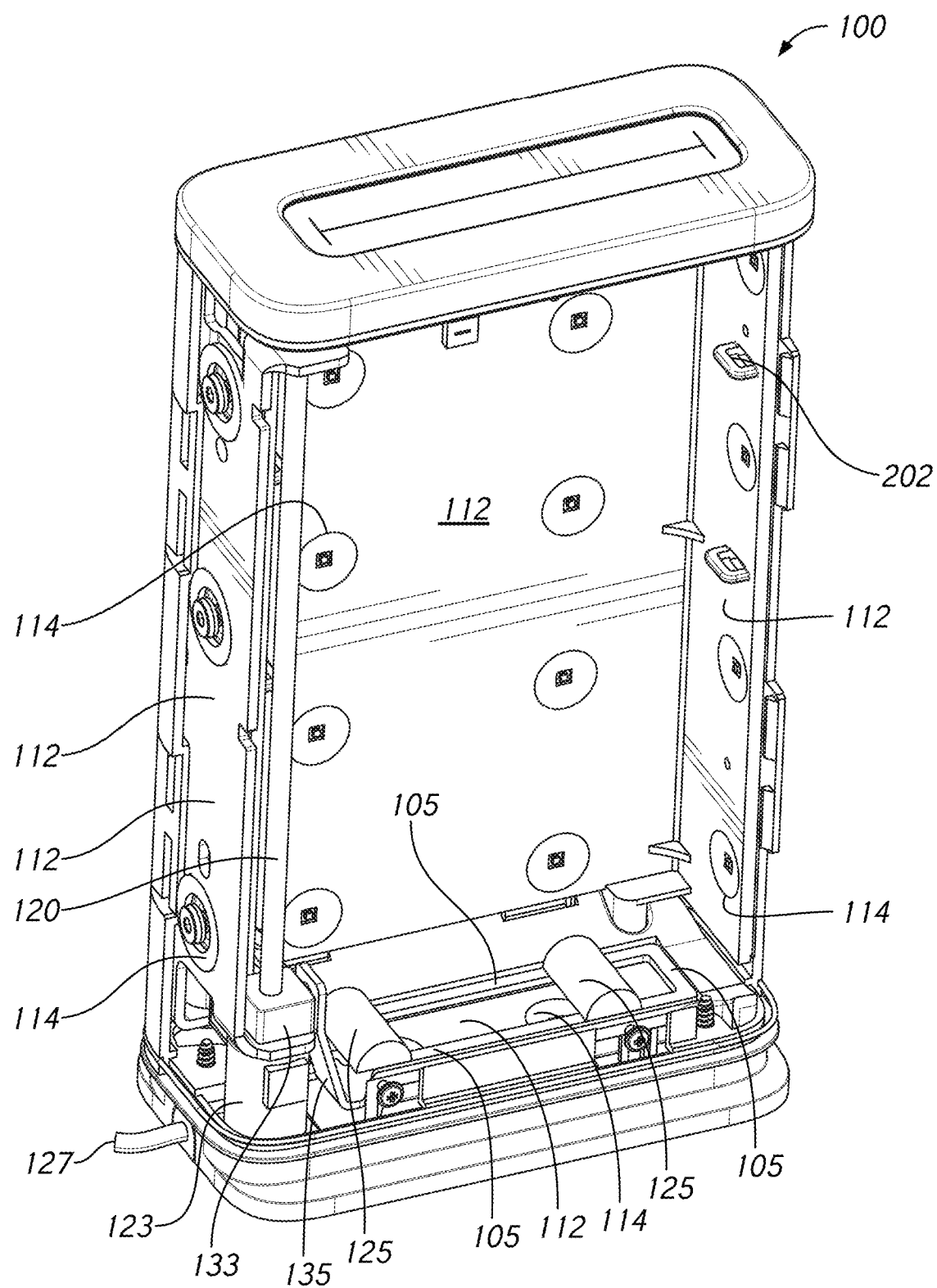
FIG. 9 is another front perspective view of the sanitizing system of FIG. 8 with a portion of the housing and other components removed.

As shown in FIG. 9, the interior of the sanitizing system 100 can include one or a plurality of sanitizing panels 112 that can include one or a plurality of radiation-emitting sources 114. One or more or all interior surfaces, such as panels 112, can comprise one or more materials that are highly reflective to sanitizing electromagnetic radiation, including any form of electromagnetic radiation disclosed in this specification, to enable uniform diffusion and scattering of sanitizing electromagnetic radiation throughout the interior chamber of the sanitizing system 100. For example, in some embodiments, one or more or all interior panels 112 can be formed of highly reflective aluminum coated walls, such as with a reflectance of at least about 0.8, at least about 0.9, and/or at least about 0.95. As with all structures and methods in this specification, the radiation-emitting sources 114 can be of a type described in any other embodiments in this specification and can function and be controlled by the processor in any manner described in any other embodiments in this specification. In some embodiments, the sanitizing system 100 includes at least five sanitizing panels 112 (e.g., front, rear, left side, right side, and bottom). In some embodiments, the sanitizing system 100 includes a sufficient number of sanitizing panels (e.g., four, five, six, etc.) to be configured to emit radiation directly or generally perpendicularly onto every side of a mobile electronic device to be sanitized, including the top surface (not shown). In some sanitizing systems 100, a top sanitizing panel (not shown) may be configured to rotate or otherwise move in and out of the path traversed by the mobile electronic device during insertion and withdrawal so as not to block the insertion or withdrawal of the mobile electronic device into or out of the sanitizing system 100.

Figure 9A:
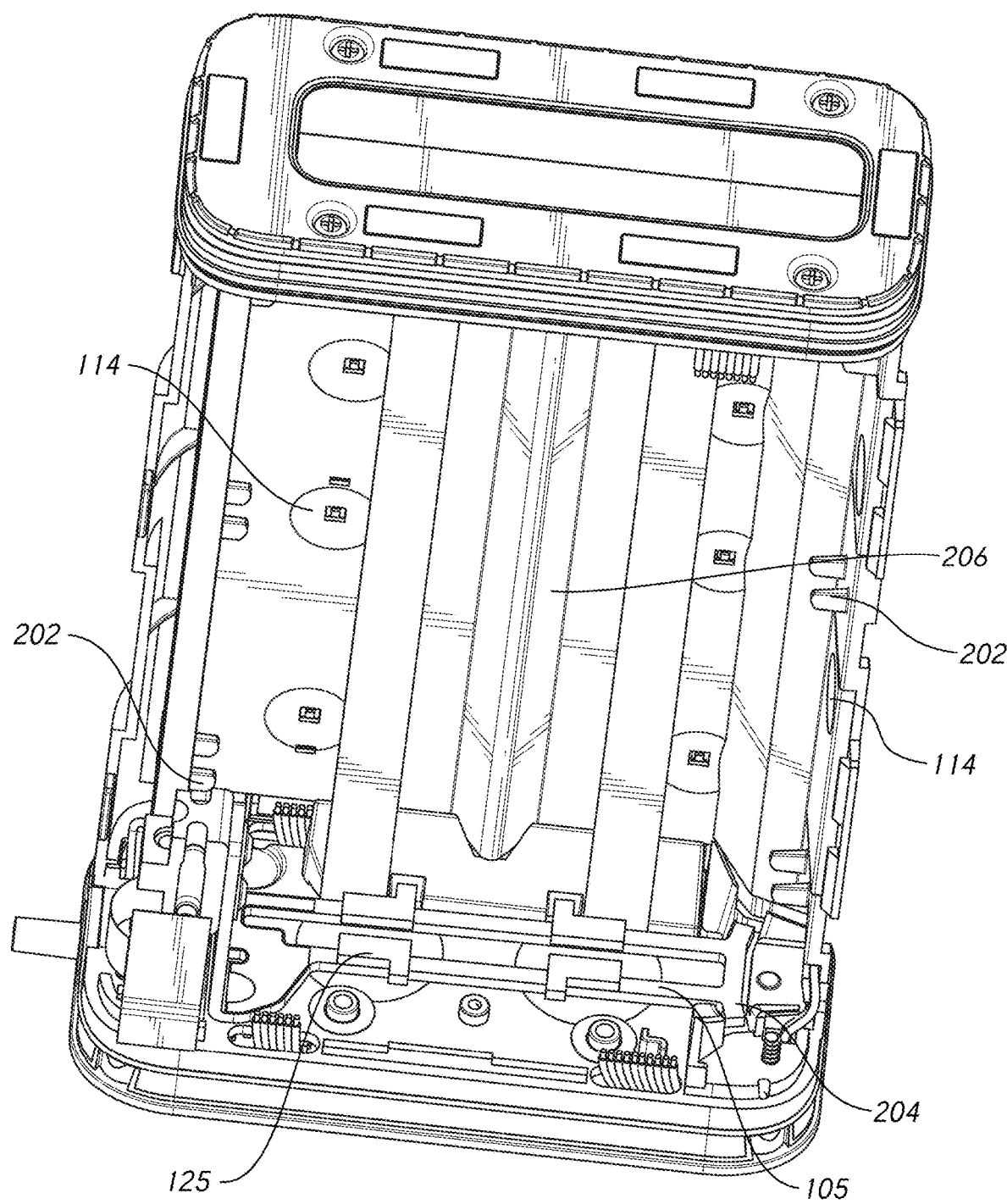
FIG. 9A is a front perspective view of another embodiment of the sanitizing system with a portion of the housing and other components removed.

FIGS. 9 and 9A also illustrates examples of components of a receiver system, which can include any of the features of the receiver system 118 of FIGS. 5-7, to help insert and withdraw the mobile electronic device 200 into and out of the sanitizer system 100. The receiver system can include a vertically moveable carriage 105 with one or more contact surfaces 125 that are generally transparent to, have high transmittance to, and/or have low attenuation of, sanitizing radiation; a conveyor 120 in the form of a threaded post and a carriage rider 133 attached to the carriage 105 via a generally perpendicular bracket 135; and an electric motor 123 that is configured to rotate the threaded post when actuated by the electronic processor 121 to move the carriage rider 133, and thereby the carriage 105, vertically up and down. The processor is configured to rotate the motor 123 in a first direction to move the carriage 105 upward and in a second, opposite direction to move the carriage 105 downward. In some embodiments, the carriage 105 can have one or more aligners 204. The one or more aligners 204 can extend from any end of the carriage 105, as shown in FIG. 9A. The aligners 204 can extend in any direction from the carriage 105. For example, perpendicular to, parallel to, or offset from the longitudinal axis of the carriage 105. The one or more aligners 204 can be positioned within a recessed area at the bottom of the interior of the sanitizing system 100 and prevent or limit the carriage 105 from turning or moving out of alignment when the carriage 105 moves upward or downward.

The sanitizing system 100 can include a power source 127, such as a power cord, a transformer, and/or a battery. The power source 127 can be used to provide electrical power for any electronic component in the sanitizing system 100, including the processor 121, the radiation-emitting sources 114, the motor 123, a user display or indicator, a speaker for communicating with a user, one or more sensors, and/or any other suitable electrical or electronic portion or component of the sanitizing system 100. In some embodiments, an exterior display or indicator can indicate or show when a sanitizing process is underway within the sanitizing system 100. For example, an external light, such as an external light band, can illuminate after a mobile electronic device 200 is inserted into the sanitizing system 100 and remain illuminated until the sanitizing process is completely and/or until the mobile electronic device 200 is at least partially positioned outside of the sanitizing system 100.

The one or more contact surfaces 125 can comprise a surface on the carriage 105 on which the lower edge or side or end of the mobile electronic device 200 is configured to rest or contact the receiver system. In some embodiments, the one or more contact surfaces 125 can extend entirely or partially across an interior gap in the carriage 105 as shown in FIG. 9. The contact surfaces 125 can comprise any suitable shape, such as a partial cylinder or half cylinder, as shown in FIG. 9. In some embodiments, the one or more contact surfaces 125 can be positioned so as not to extend partially or entirely across an interior gap in the carriage 105. For example, in some embodiments, the contact surfaces 125 can comprise one or more spacers positioned on top and/or extending away from the carriage 105, such as one or more spacers with an angled portion, a first portion that is generally perpendicular to a second portion, and/or an L-shaped piece, as shown in FIG. 9A. The one or more spacers can allow radiation emitted from one or more sanitizing sources 114 positioned under the carriage 105 to transmit radiation upwardly through the gap in the carriage 105 unimpeded or without substantial resistance or attenuation from the contact surfaces 125. In some embodiments, the L-shaped contact surfaces 125 do not cross over the open space in the carriage 105. A first portion of the L-shaped contact surfaces 125 can be positioned above the carriage 105 and a second portion of the L-shaped contact surfaces can extend away from the carriage 105 forming a generally L-shape. The contact surfaces 125 can be formed of a material that is substantially transparent to sanitizing radiation (including any or all types of sanitizing radiation disclosed in this specification) and/or the contact surfaces 125 can be shaped and/or oriented such as to convey sanitizing radiation from a side of the carriage 105 to or toward a bottom surface of the mobile electronic device 200. In some embodiments, the one or more contact surfaces 125 can be made of a material that is: (a) sufficiently rigid to hold the weight of a mobile electronic device without bending, cracking, or breaking; (b) sufficiently scratch-resistant to avoid damaging the surface of the contact surface 125 through contact with the mobile electronic device 200; (c) sufficiently transparent to UV or other sanitizing radiation to avoid significantly impeding or obstructing the radiation emitted from the sources 114 from impinging on the underside of the mobile electronic device 200; and/or (d) shaped in such a way as to diminish the contact area between the contact surface 125 and the mobile electronic device 200 and/or to help spread or focus radiation in a helpful manner, such as by providing a first generally flat or planar lower side and a second generally curved or arcuate upper side, as shown. In some embodiments, the one or more contact surfaces 125 are made of fused silica, quartz, glass, acrylic, and/or plastic. In some embodiments, the one or more contact surfaces 125 are transparent or clear acrylic. In some embodiments, the receiver system supports the bottom of the mobile electronic device 200 only through contact with the one or more contact surfaces 125.

In some embodiments the sanitizing system 100, can include one or more supports 202, as shown in FIGS. 9 and 9A. The supports 202 can help guide the mobile electronic device 200 into the sanitizing system 100. The supports 202 can help keep the mobile electronic device 200 offset from the interior panels 112. The supports 202 can have rounded or non-sharp or non-pointed edges to prevent damage from occurring to the mobile electronic device 200. In some embodiments, the supports 202 can be oriented generally horizontally, as shown in FIG. 9. The horizontal supports 202 can have a width that is larger than a height. In some embodiments, the supports 202 can be oriented generally vertically, as shown in FIG. 9A. The vertical supports 202 can have a height that is larger than a width. The use of vertical supports 202 can allow the majority of the radiation that is emitted by sanitizing sources 114 and transmitted along the interior walls of the sanitizing system 100 to pass by the supports 202 from the radiation emitting sources 114 to the mobile electronic device 200.

The sanitizing system 100, can also include a light or radiation directing structure 206, as shown in FIG. 9A. The radiation directing structure 206 can help direct the radiation or sanitizing light from the radiation emitting sources 114 on sides of the sanitizing system towards the middle of the mobile electronic device 200. The radiation directing structure 206 can increase the consistency of sanitizing coverage by scattering the radiation or sanitizing light across more angles. As shown in FIG. 9A, the light or radiation directing structure 206 can extend vertically in the sanitizing system 100. The light or radiation directing source can have two portions forming an acute angle or generally V-shaped cross-section as shown in FIG. 9A. In some embodiments, the sanitizing panels 112 can be made of or be coated with a highly reflective surface material, such as aluminum, for reflecting sanitizing light or radiation.

Figure 10:
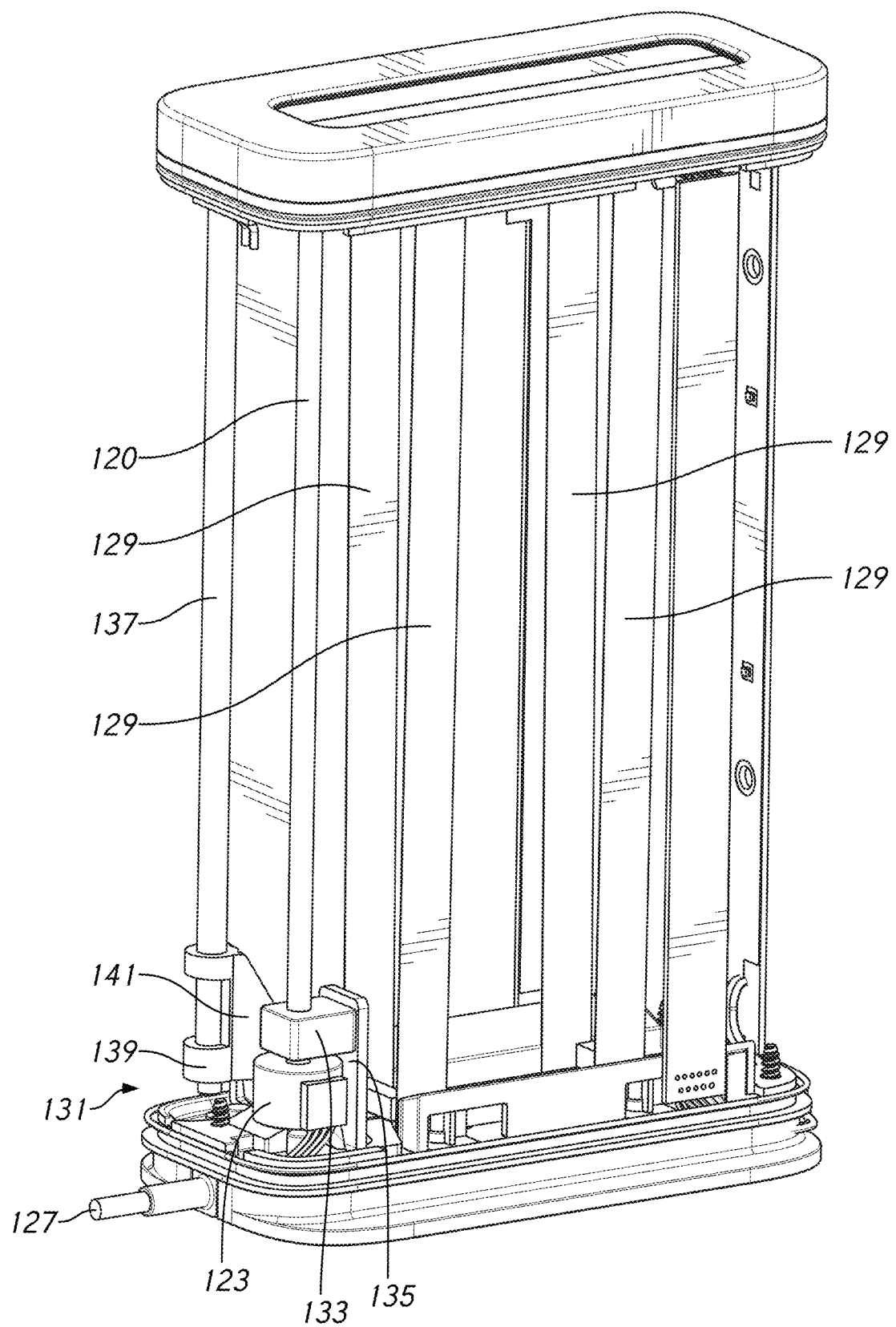
FIG. 10 is another front perspective view of the sanitizing system of FIG. 8 with a portion of the housing and other components removed but with additional portions of the conveyor system visible.
Figure 10A:
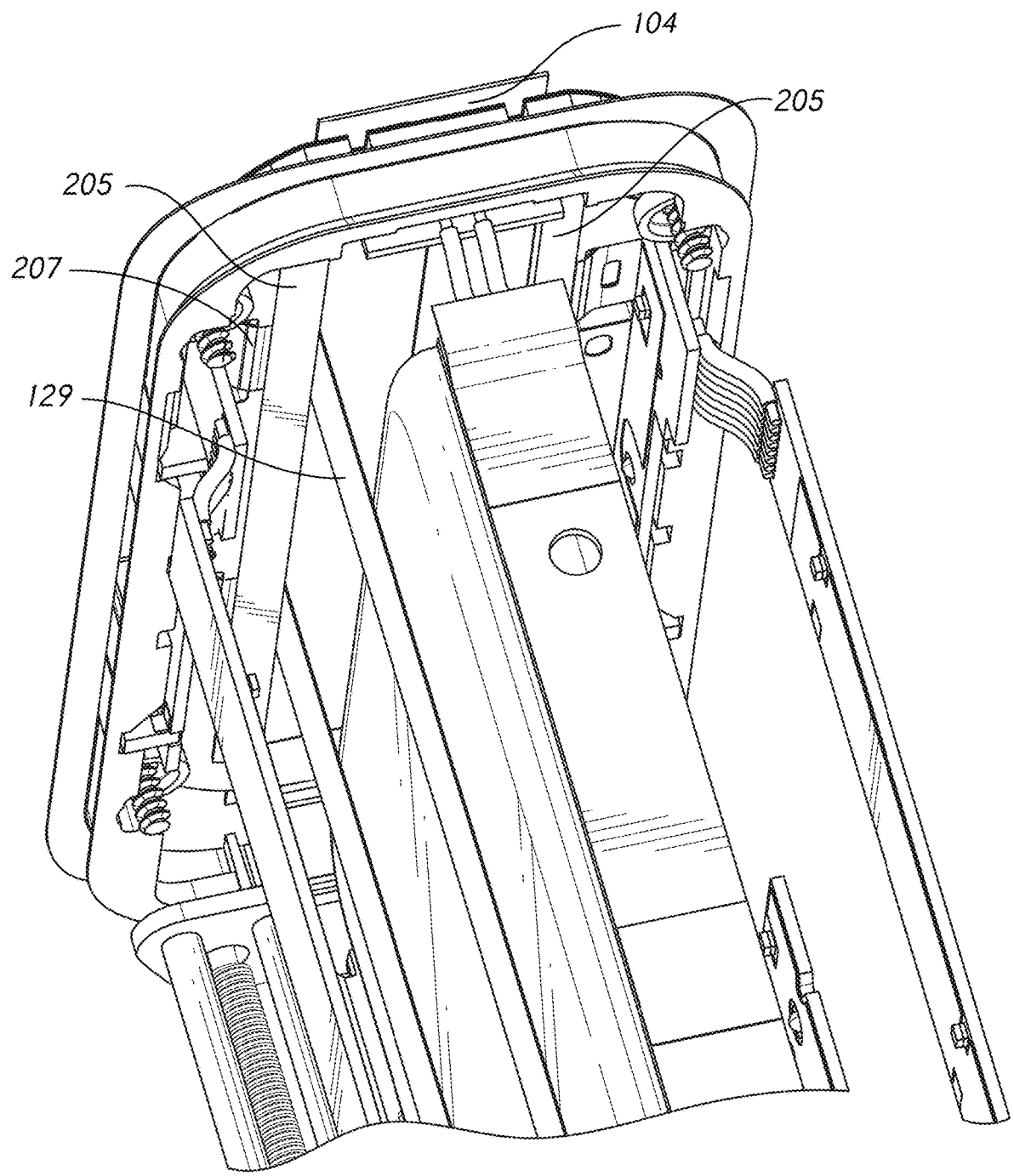
FIG. 10A is a side perspective view of the sanitizing system of FIG. 8 with a portion of the housing and other components removed but with additional portions of the conveyor system in view.
Figure 11:
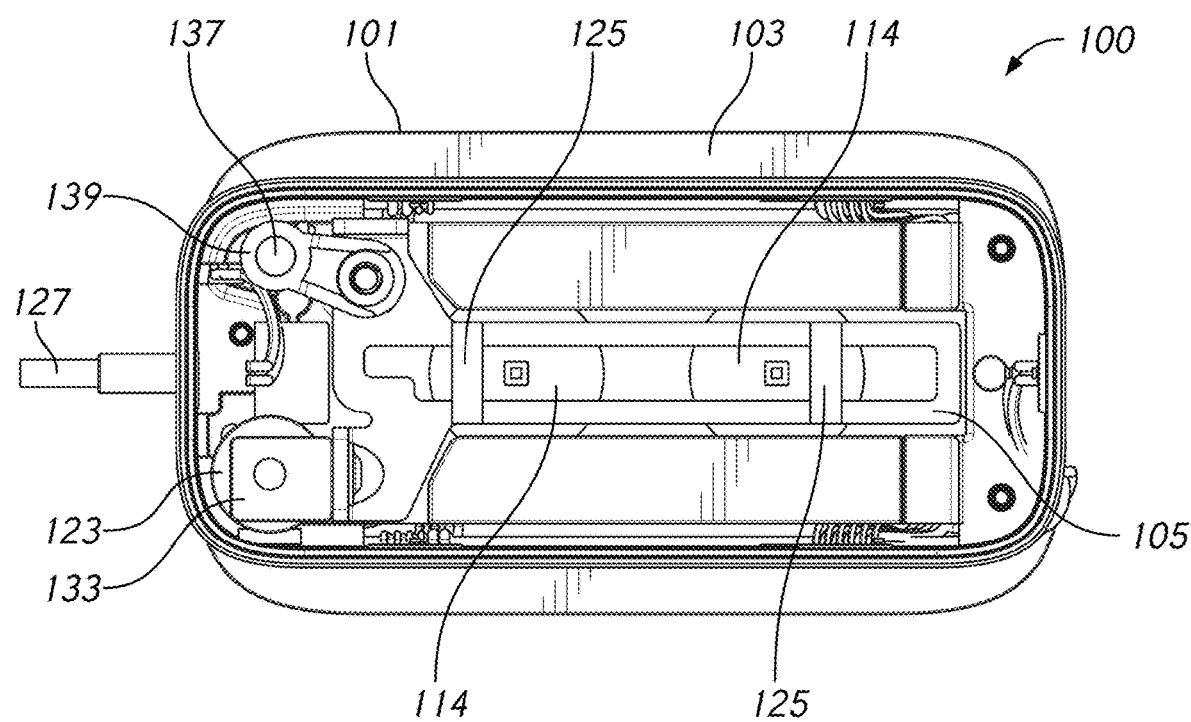
FIG. 11 is a top view of the sanitizing system of FIG. 8 with a portion of the housing and other components removed.

As illustrated in FIGS. 10, 10A and 11, in some embodiments, the conveyor system 120 can include one or more holders 129 and one or more stabilizers 131. In some embodiments, the holders 129 comprise one or more generally vertically oriented barriers, braces, or supports configured to assist in the insertion and withdrawal of the mobile electronic device 200 into the interior cavity of the sanitizing system 100. As shown, the holders 129 can comprise one or a plurality of strips, sheets, bars, walls, strands, wires, netting, or other substance or structure to help align, direct, and/or guide the mobile electronic device 200 in a generally linear, generally vertical direction, and/or to help hold or restrain the mobile electronic device 200 when inserted or during emission of radiation to a degree that the mobile electronic device 200 does not contact other front, rear, and/or lateral surfaces or structures within the cavity of the sanitizing system 100 and/or to resist tipping, tilting, lodging, or wedging of the mobile electronic device 200 within the cavity of the sanitizing system 100. In some embodiments, as illustrated, one or more of the holders 129 are substantially flat or substantially planar; and in some embodiments, at least a portion of one or more of the holders 129 are curved, arcuate, or bent. In some implementations, by providing a curved, arcuate, or bent shape for one or more of the holders 129, the transmission, emission, or communication of radiation can be controlled or modified in one or more desirable ways. As illustrated, in some embodiments, the one or more holders 129 can be provided on front and rear sides of the interior space of the sanitizing system 100, with the lateral left and right lateral sides of the interior space unimpeded by and free from holders 129; and in some embodiments, the one or more holders 129 can be provided additionally or only on left and/or right lateral sides of the interior space of the sanitizing system 100, with the front and rear sides of the interior space unimpeded by and free from holders 129.

In some embodiments, as illustrated, the top and bottom ends of the holders 129 are affixed to rigid portions of the sanitizing system 100 so that the holders 129 remain securely in place within the cavity of the sanitizing system 100. The holders 129 can be rigid, generally rigid, flexible, and/or elastomeric. In some embodiments, the holders 129 can be secured in place by the use of one or more securing pieces 205. The holders 129 can extend vertically in the sanitizing system 100 and wrap over the one or more securing pieces to a second position 207, as shown in FIG. 10A. In some embodiments, one or more securing pieces 205 can be made of foam. The one or more securing pieces can also assist the enclosure 104 to stay shut by applying an upward force to close the enclosure 104 which can help to prevent radiation from escaping the sanitizing system 100. The one or more securing pieces can act as blockers of radiation such that the sanitizing system 100 resists the emission of sanitizing radiation outside of the housing of the sanitizing system 100. In some embodiments, the holders 129 can be generally transparent with respect to the type of radiation emitted from the radiation-emitting sources 114 (examples of which are described elsewhere in this specification) so that the holders 129 permit radiation to pass through them and do not appreciably obstruct radiation emitted by the sources 114 from impinging upon the portions of the surfaces of the mobile electronic device 200 that are positioned on the opposite sides of the holders 129 from the radiation-emitting sources 114. As shown, the holders 129 can comprise multiple strips; however, in some embodiments, the holders 129 can comprise sheets of material or any other suitable holding or retaining structure, such as generally horizontally oriented strips or sheets, or a single strip or sheet. In some embodiments, the strip or sheet or other form of holders 129 can be folded, formed in a sleeve or tube, or otherwise configured to generally surround or envelop the mobile electronic device 200 when it is inserted fully into the sanitizing system 100.

The one or more holders 129 in any embodiment of this specification can be made of or can comprise a polymeric film, such as a propylene film. The film can comprise a halogen, such as fluorine. For example, the one or more holders 129 can be made of or can comprise a fluorinated ethylene propylene film. In some embodiments, the one or more holders 129 are made from a film that is very thin. For example, the thickness of the film can be less than or equal to about 750μ or less than or equal to about 500μ. In some embodiments, the thickness of the film can be at least about 50μ or at least about 10μ.

In some embodiments, the one or more holders 129 can be made of or can comprise plastic, glass, fused silica, quartz, and/or metal (e.g., metal netting, wiring, or perforated metal). In some embodiments, the one or more holders 129 can be made of or comprise a film, such as a polymer film, with one or more of the following characteristics: (a) high optical transmittance for ultraviolet or other sanitizing radiation (examples of which are described elsewhere in this specification) so as not to obstruct the sanitizing radiation from impinging upon the mobile electronic device to an effective degree (e.g. the film can have an optical transmittance that permits radiation emitted by the sanitizer to pass through the film with sufficient intensity to effectively sanitize the mobile electronic device, such as a transmittance of at least about 75% or at least about 85% for any wavelengths between about 100 nm and about 400 nm); (b) low coefficient of friction such as to resist obstructing the insertion or withdrawal of the mobile electronic device (e.g., a coefficient of friction that is sufficiently low so as to be configured to permit the mobile electronic device 200 to smoothly slide along at least a portion of the film, or to permit the film to be moved by the motor, without causing the film to substantially stretch, tear, wrinkle, or fold, such as a coefficient of friction that is less than or equal to about 0.5 or less than or equal to about 0.3); (c) high durability so as not to tear, wrinkle, or scratch during repeated insertions and withdrawals of mobile electronic devices; (d) high dimensional stability after repeated exposure to ultraviolet or other sanitizing light; (e) high dimensional stability within temperature ranges common to human climates or living spaces (e.g., between about 50 degrees Fahrenheit and about 120 degrees Fahrenheit, or between about 60 degree Fahrenheit and about 90 degrees Fahrenheit); (f) low absorption of liquids such as water and oil so as to resist transfer of contaminants from a mobile electronic device onto the holders 129 during insertion and withdrawal of mobile electronic devices (e.g., weight increase of less than or equal to about 1% or less than or equal to about 0.1% when immersed in water for an extended period); (g) low adhesion to mobile electronic devices; and/or (h) low chemical reactivity or high chemical inertness so as not to react appreciably in the presence of sanitizing radiation and/or with contaminants commonly found on mobile electronic devices (such as oils or sweat from human hands). In some embodiments, one or more of the holders 129 or a portion thereof is substantially entirely free from plasticizers.

As shown in FIG. 10, the stabilizer 131 can help to provide generally stable, generally straight, and/or generally linear vertical movement of the carriage 105 as it advances up and down during insertion and withdrawal of the mobile electronic device. For example, the stabilizer 131 can resist the creation of an appreciable sway or rotation on the carriage 105 which might otherwise unduly increase the friction of the carriage rider 133 against the threaded post, unduly increase the friction of the mobile electronic device 200 against the one or more holders 129, and/or allow the mobile electronic device 200 to tilt, lodge, snag, or wedge into or contact one or more other structures inside the cavity of the sanitizer system 100.

In some embodiments, as illustrated, the stabilizer 131 can comprise an elongate non-rotational, fixed post 137 with a smooth, low-friction exterior surface that is oriented generally vertically and generally parallel to and spaced apart from the threaded post of the conveyor 120. A stabilizing rider 139 is configured to move or glide vertically up and down along the fixed post 137. The stabilizing rider 139 can comprise one or more rings partially or entirely surrounding the fixed post 137. The stabilizing rider 139 is attached to the carriage rider 133 by way of a stabilizing bracket 141. As the carriage rider 133 is advanced up and down along the threaded post by the rotation of the motor 123, an upward or downward force is conveyed through the stabilizing bracket to the stabilizing rider 139, advancing it up and down in tandem with the carriage rider 133. The coupling between the carriage rider 133 and the stabilizing rider 139 is configured to resist any significant lateral movement of the carriage rider 133 along the conveyor 120 in response to any torque that may be applied during normal operation of the receiver system.

Figure 12:
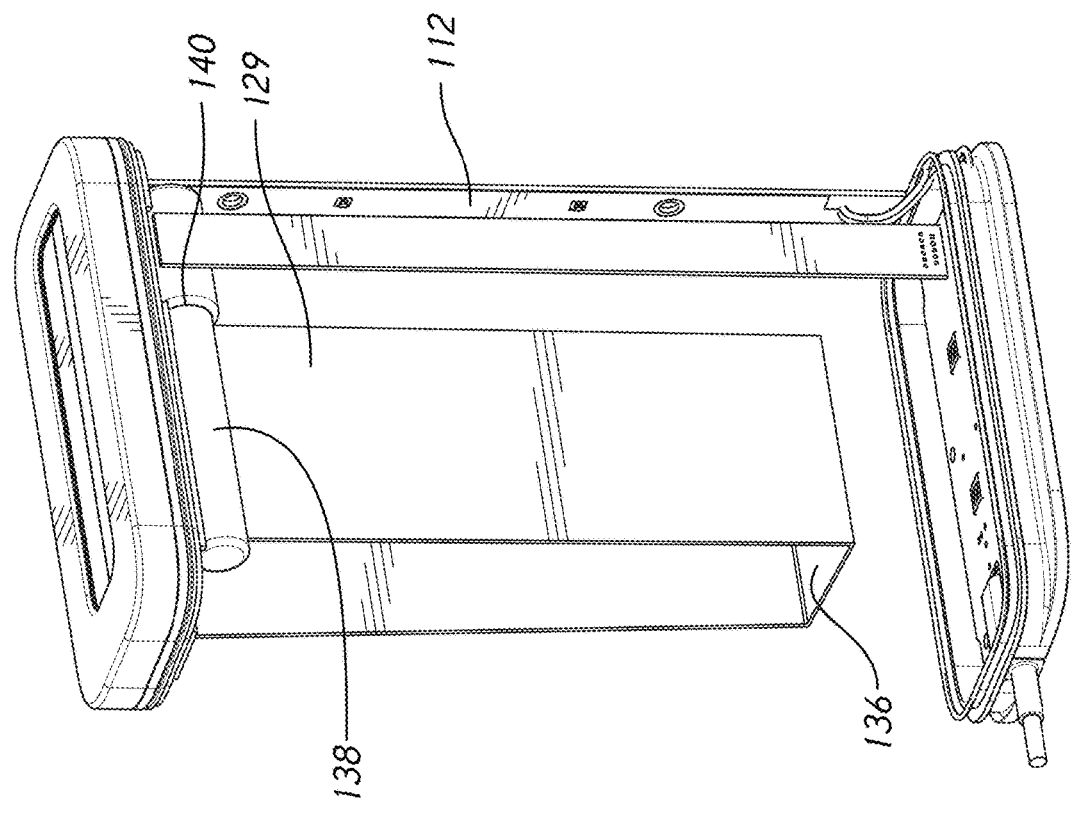
FIG. 12 a front perspective view of another embodiment of the example of the sanitizing system of FIG. 8 with a portion of the housing and other components removed.
Figure 12:
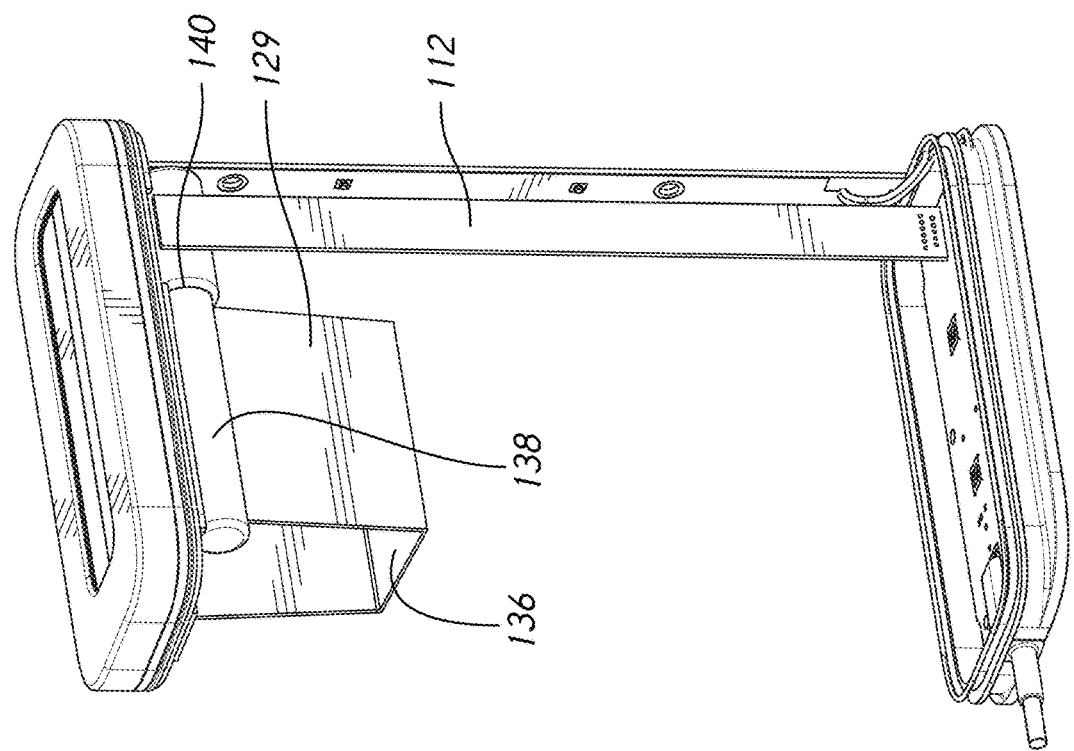

As shown in FIG. 12, in some receiver systems, the one or more holders 129 can be moved or adjusted to modify the amount of surface area or length that is accessible for contact with or transportation of a mobile electronic device. For example, the one or more holders 129 can be provided in the form of a sheet, straps, netting, or wires that can be disposed partially within the open space of the cavity within the housing 101 between a first region that is fixed to one side of the upper interior region of the housing 101 and a second region that is partially stored on a spool 138 on an opposite upper interior region of the housing 101. The one or more holders 129 can extend between the first and second regions to form a cradle 136 of variable length or surface area to hold, receive, and/or transport mobile electronic device 200. The spool 138 can be rotatable by a cradle motor 140 under the control of the electronic processor 121. The one or more holders 129 can be selectively deployed by rotating the cradle motor 140 to spool out additional length or surface area of the one or more holders 129 or retracted by rotating the cradle motor 140 in the opposite direction to spool in length or surface area of the one or more holders 129.

In the example of FIG. 12, before insertion of the mobile electronic device 200 into the sanitizing system 100, an initial section of the one or more holders 129 is available for contact with the mobile electronic device 200 when inserted into the housing 101. After the mobile electronic device 200 is inserted through the top opening, the cradle motor 140 can rotate the spool 138 to deploy more area or length of the holder 129 downward into the open space of the housing 101, causing the cradle 136 formed by the one or more holders 129 to lengthen, thereby lowering the mobile electronic device 200 further into the bottom region of the open space within the housing 101. After sanitizing, the spool 138 can be rotated in the opposite direction by the cradle motor 140 under the control of the processor to spool in at least a portion of the holder 129, thereby raising the mobile electronic device 200 and moving it outside of the housing 101 to be retrieved by a user.

Figure 13:
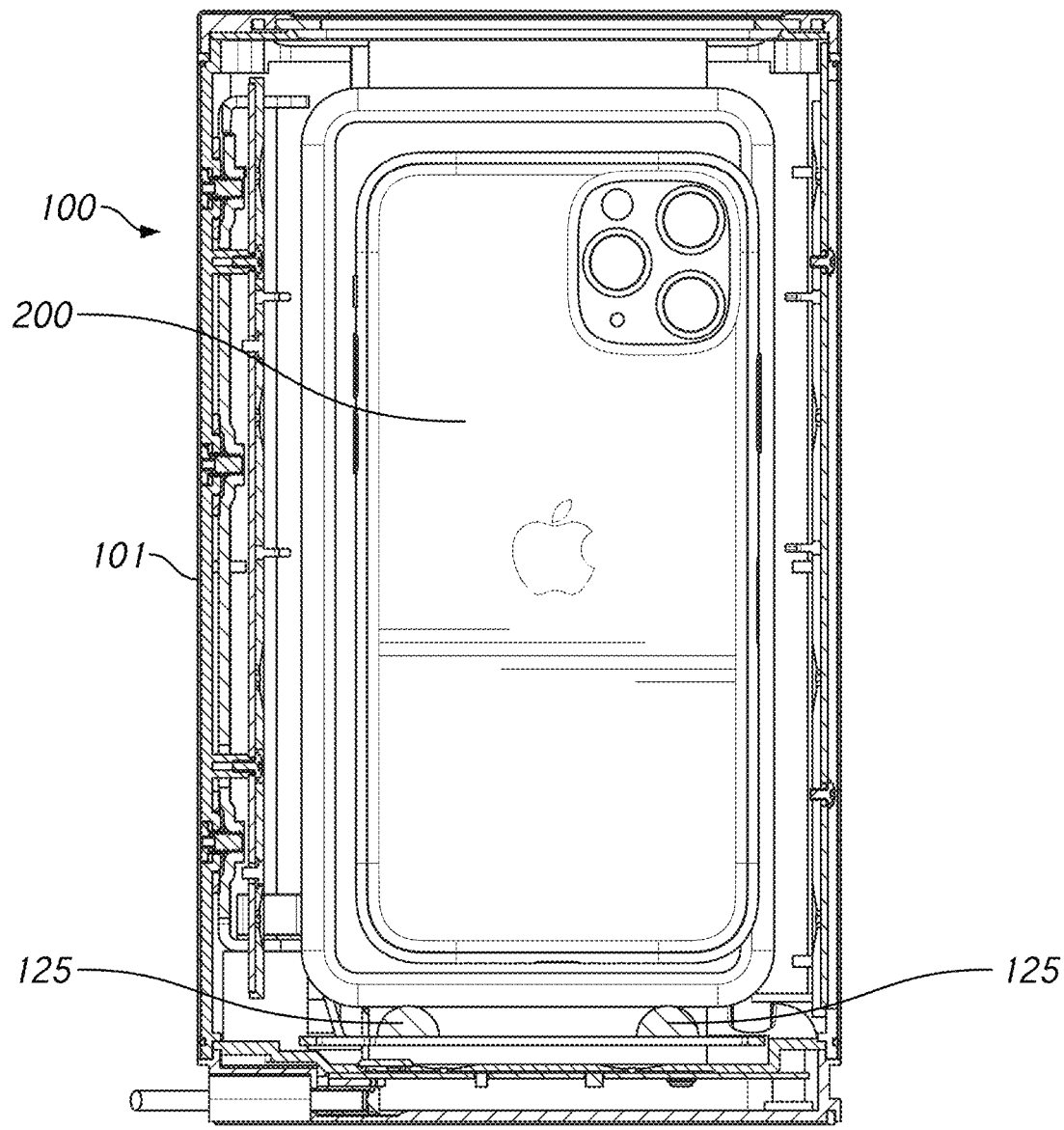
FIG. 13 is a front view of the example of the sanitizing system of FIG. 8 with an example of a mobile electronic device positioned inside and with a portion of the housing and other components removed.

As illustrated in FIG. 13, in any embodiment, when the receiving system has moved the mobile electronic device 200 fully into the interior of the housing 101, there can be sufficient space around the mobile electronic device 200 to avoid contact between the mobile electronic device 200 and interior surfaces inside of the sanitizing system 100, besides the one or more holders 129 (not shown in this figure) and the one or more contact surfaces 125. When the sanitizing process is complete, as carried out in accordance with any embodiment or description in this specification or otherwise, the receiving system is configured to advance the mobile electronic device 200 upward and out through the opening in the top of the sanitizing system 100 to be retrieved by a user.

Figure 14:
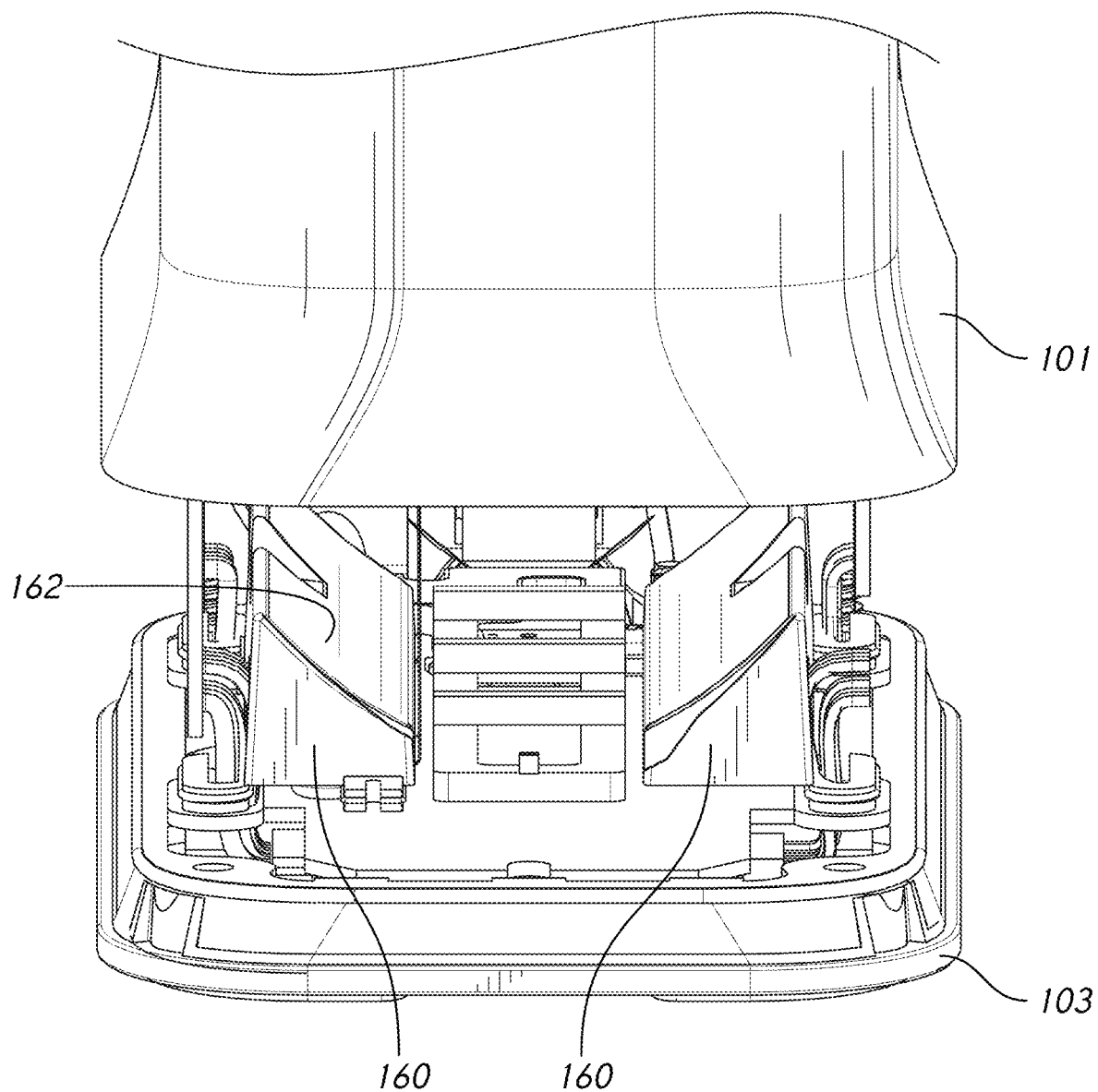
FIG. 14 is a partial interior perspective view, showing components toward the base of an example sanitizing system.

FIG. 14 shows a housing 101 that has been raised to reveal some inside structures. Two reflector supports 160 are positioned on either side or both sides of where a carriage 105 can lower a mobile electronic device 200 into a lower region of a sanitizing system 100 near the base 103. The top, curved surface of these supports comprises a reflector 162. Each reflector 162 can be a film or surface that reflects radiation generally toward the device 200 to assist in providing coverage and sanitation. The reflectors 162 can comprise reflecting surfaces configured to distribute radiation (e.g., UV-C). The reflectors 162 can be made of a thin sheet, such as a reflective metallic material (e.g., aluminum foil) and/or a film. The supports 160 can have a void or hollow underneath which can contain or cover other physical or electrical components of the system 100. The supports 160 can be solid and formed from a rigid or resilient material. They can be glued or screwed into place, for example. They can have generally concave or parabolic surfaces configured to aim light generally at a device 200 to be sanitized. The supports 160 can have a lower, inward height that corresponds generally to the height of the carriage 105 (see FIG. 9) when a device 200 is lowered into the system 100. The supports 160 can have a higher, outward height and a reflector 162 can extend between the lower and higher heights. The supports 160 can also perform a physical centering function. If an electronic device 200 is displaced from the carriage 105, these supports can tend to shift that device back onto the carriage 105.

Thus, in some embodiments, the sanitizing system 100 can comprise at least one reflector positioned and shaped to reflect sanitizing radiation back toward the mobile electronic device. For example, one or more radiation-emitting sources 114, such as one or more LEDs (light-emitting diodes), may be positioned to emit directly toward flat surfaces of a device to be sanitized. Each of the one or more LEDs can comprise a generally circular reflector with a diode positioned generally in the center. In some embodiments, separated from or integrated with an LED, one or more reflectors can be positioned to generally face a corner or edge of the device, thereby directing toward corners or edges of the device radiation from radiation emitting sources 114 that face flat surfaces of the device.

Figure 15:
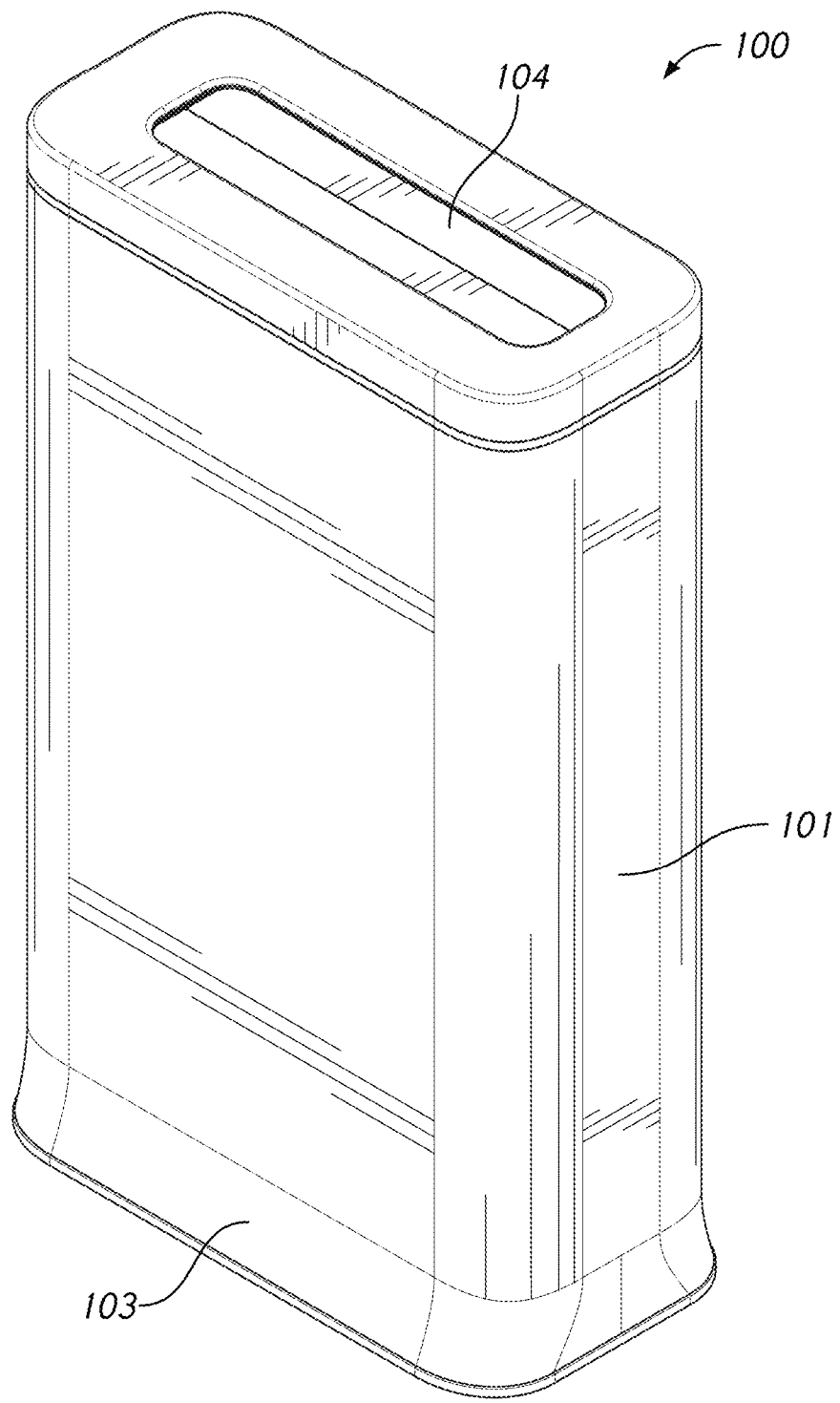
FIG. 15 shows a perspective view of the outside of a sanitizing system embodiment.
Figure 16:
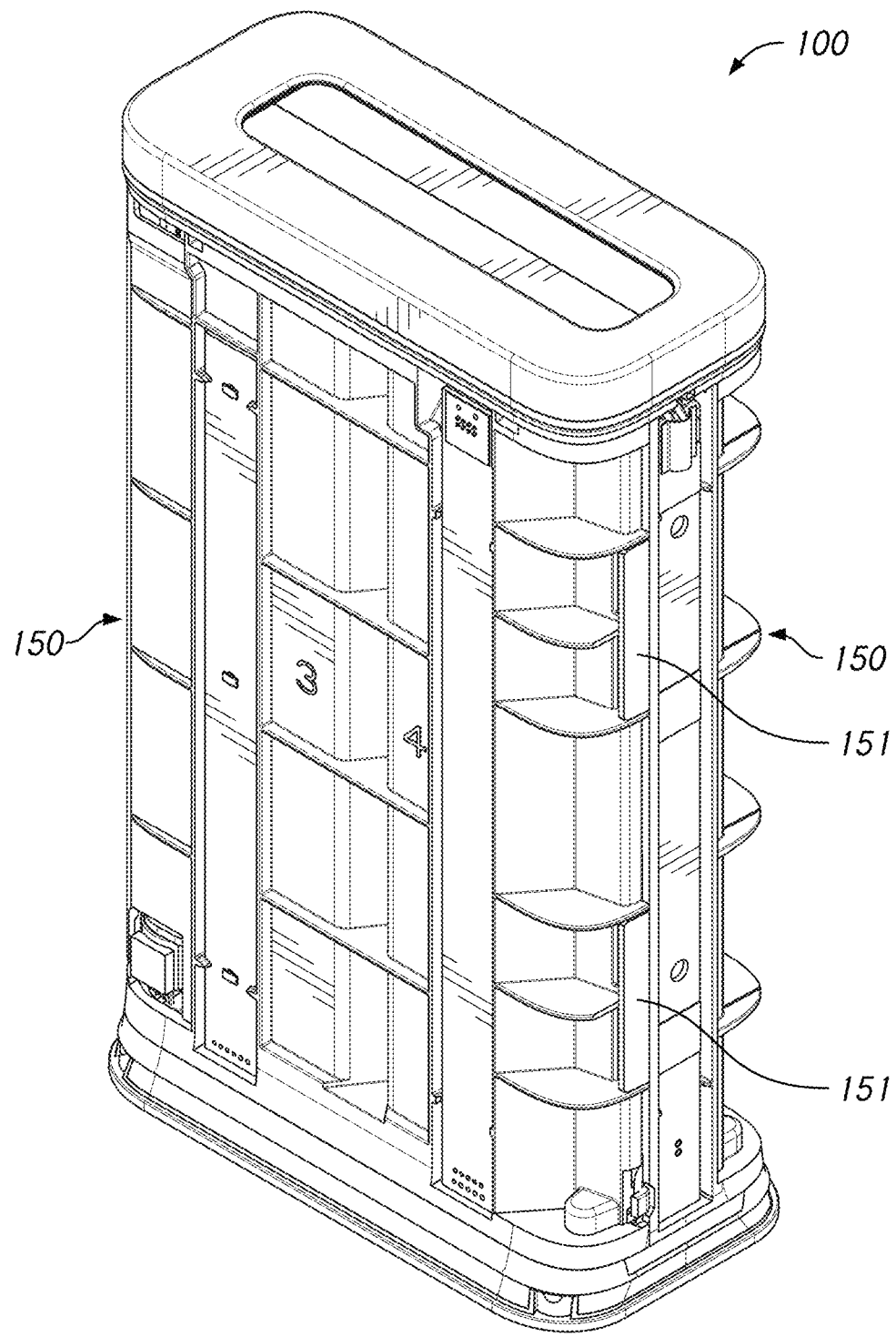
FIG. 16 shows the embodiment of FIG. 15, with an outer cover removed.
Figure 17:
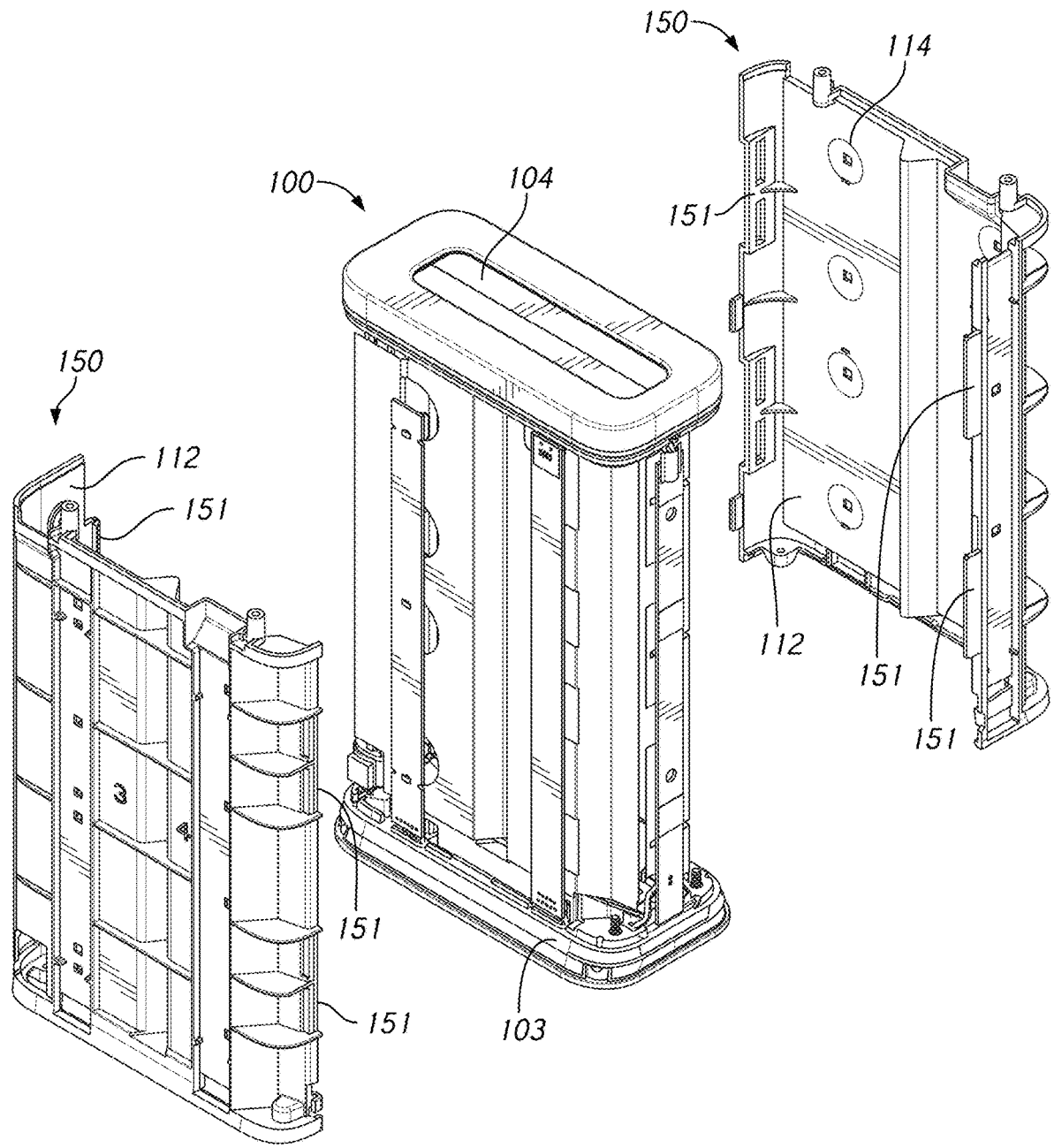
FIG. 17 shows the embodiment of FIGS. 15 and 16, with wall structures separated.

Another example of a sanitizing system 100 is illustrated in FIGS. 15-17. FIG. 15 shows the outer contours of an embodiment of a sanitizing system 100. As shown in FIG. 15, the housing 101 can comprise a height measurement that is substantially larger than its width or depth measurements. In some embodiments, the dimensions of the housing 101 (e.g., width, depth, and/or height) can each be no more than about 20% larger or no more than about 50% larger than each of the dimensions of the types of mobile electronic devices that are intended to be sanitized by the sanitizing system 100.

The housing 101 can comprise a base 103 positioned at the bottom of the housing. As shown, the base 103 can comprise an outwardly tapering width that increases as the base 103 extends down from the housing 101. The increase in width of the base 103 can create a curved appearance. The enclosure 104 can be located in a non-flush recessed position with respect to an upper portion of the housing 101.

The housing 101 of the sanitizing system 100 comprises an enclosure with six sides: a top, a bottom, a left side, a right side, a front side, and a rear side. As shown, the opening to receive and eject the mobile electronic device 200 is provided on only a single side. The opening can be provided on any single side or can span multiple sides. In some embodiments in which the opening is provided on only a single side, the interior of the sanitizing system 100 can be maintained in a more sanitary, debris-free, and otherwise protected condition than when the entire interior of the housing is exposed when opening up and inserting or retrieving the mobile electronic device 200 from within the sanitizing system 100, such as in a hinged clam-shell type housing arrangement where a user's fingers are likely to touch the interior of the sanitizing system 100.

In the illustrated embodiments, the housing 101 can remain generally or substantially closed even when the mobile electronic device 200 is inserted or ejected from the housing 101, by virtue of the single-side opening and the closeable opening with the outer enclosure 104. In some embodiments, as shown, the user's experience with the device is made easier by permitting the user to simply activate the sanitizing system 100 by pushing a mobile electronic device 200 into the single-side opening and retrieving the mobile electronic device 200 from the same single-side opening when the sanitizing process is complete and the mobile electronic device 200 is ejected, without requiring the user to manually open the housing 101, precisely position the mobile electronic device 200 within the cavity of the housing 101, and/or manually close the housing 101.

FIG. 16 shows the embodiment of FIG. 15, with an outer cover removed to reveal structural features. The embodiment can include wall structures 150. The wall structures 150 can comprise two parts, as shown in FIG. 17. While two wall structures 150 are illustrated, any number of wall structures 150 can be used. For example, 1, 2, 3 or more wall structures 150 can be used. The wall structures 150 provide support for the sanitizing system 100 and can protect the interior features. In some embodiments, the wall structures 150 can be coupled via overlapping pieces 151. The overlapping pieces 151 can include corresponding recesses and protrusions as shown in FIG. 17. Other suitable coupling methods can also be used. The wall structures 151 can be positioned between the first outer enclosure 104 and the base 103. FIG. 17 shows the same embodiment, with wall structures 150 separated to reveal additional interior features. For example, FIG. 17 illustrates the radiation-emitting sources 114 and the one or more sanitizing panels 112.

Figure 18:
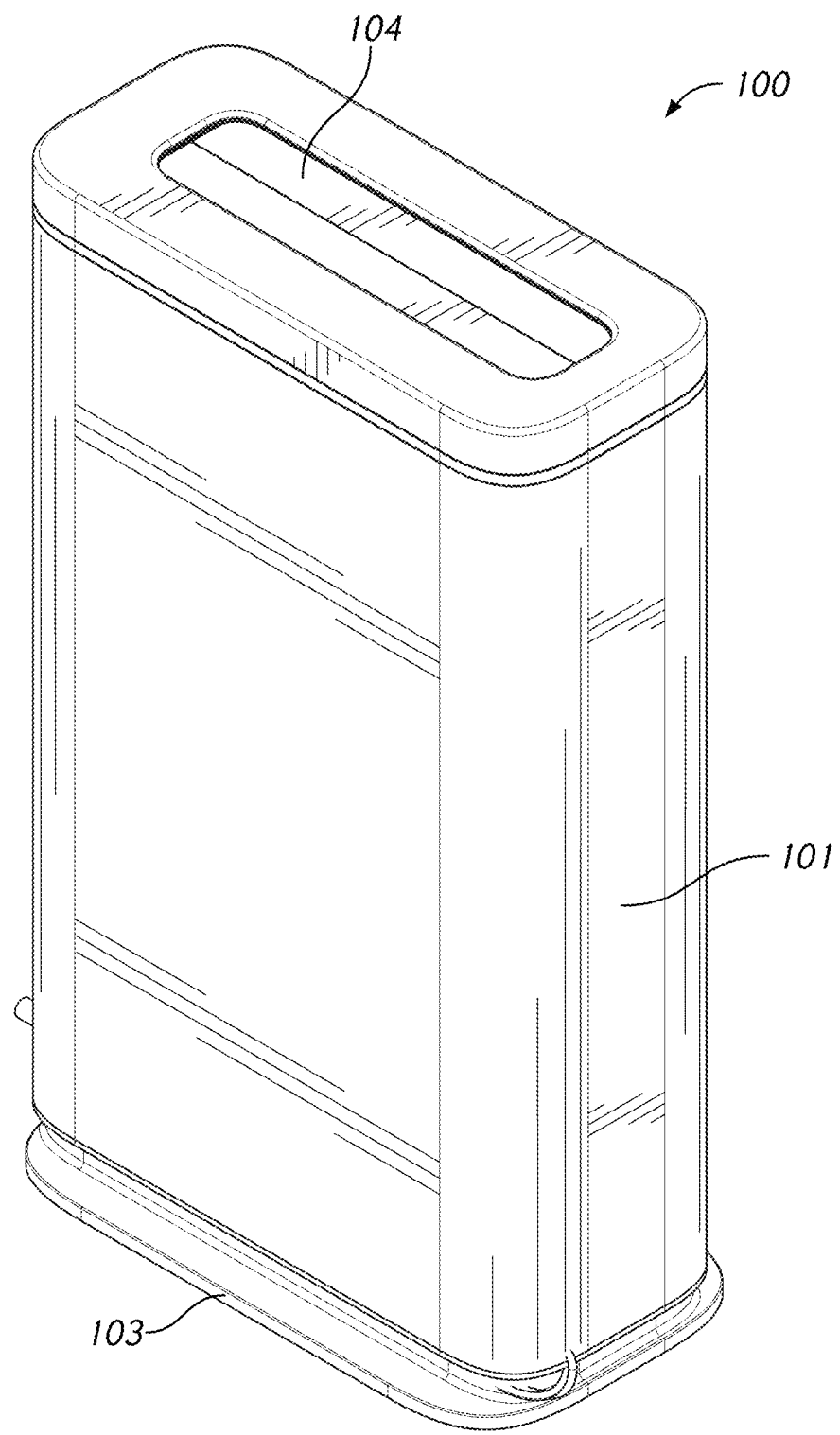
FIG. 18 shows a perspective view of another embodiment of a sanitizing system.
Figure 19:
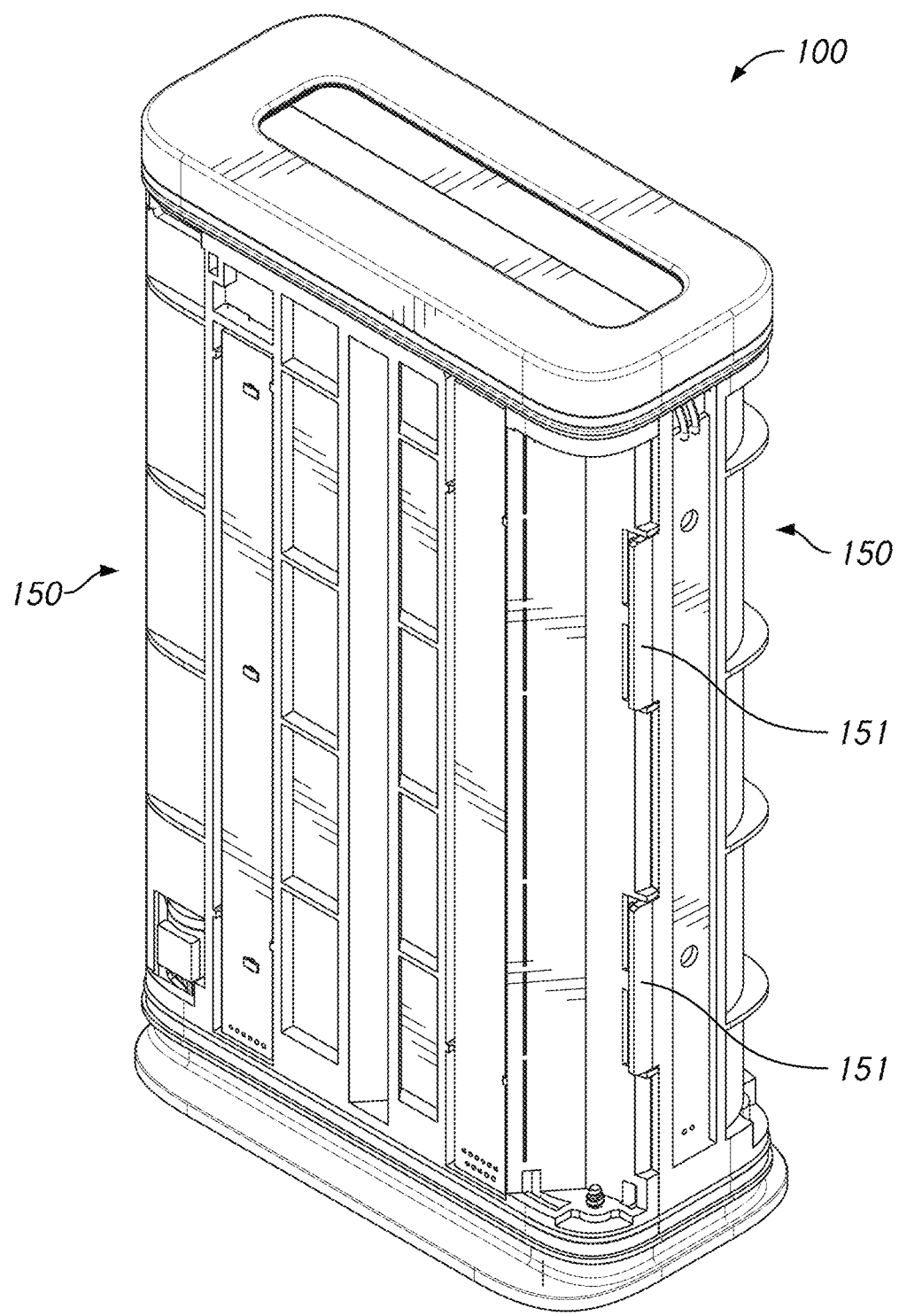
FIG. 19 shows the embodiment of FIG. 18, with an outer cover removed.
Figure 20:
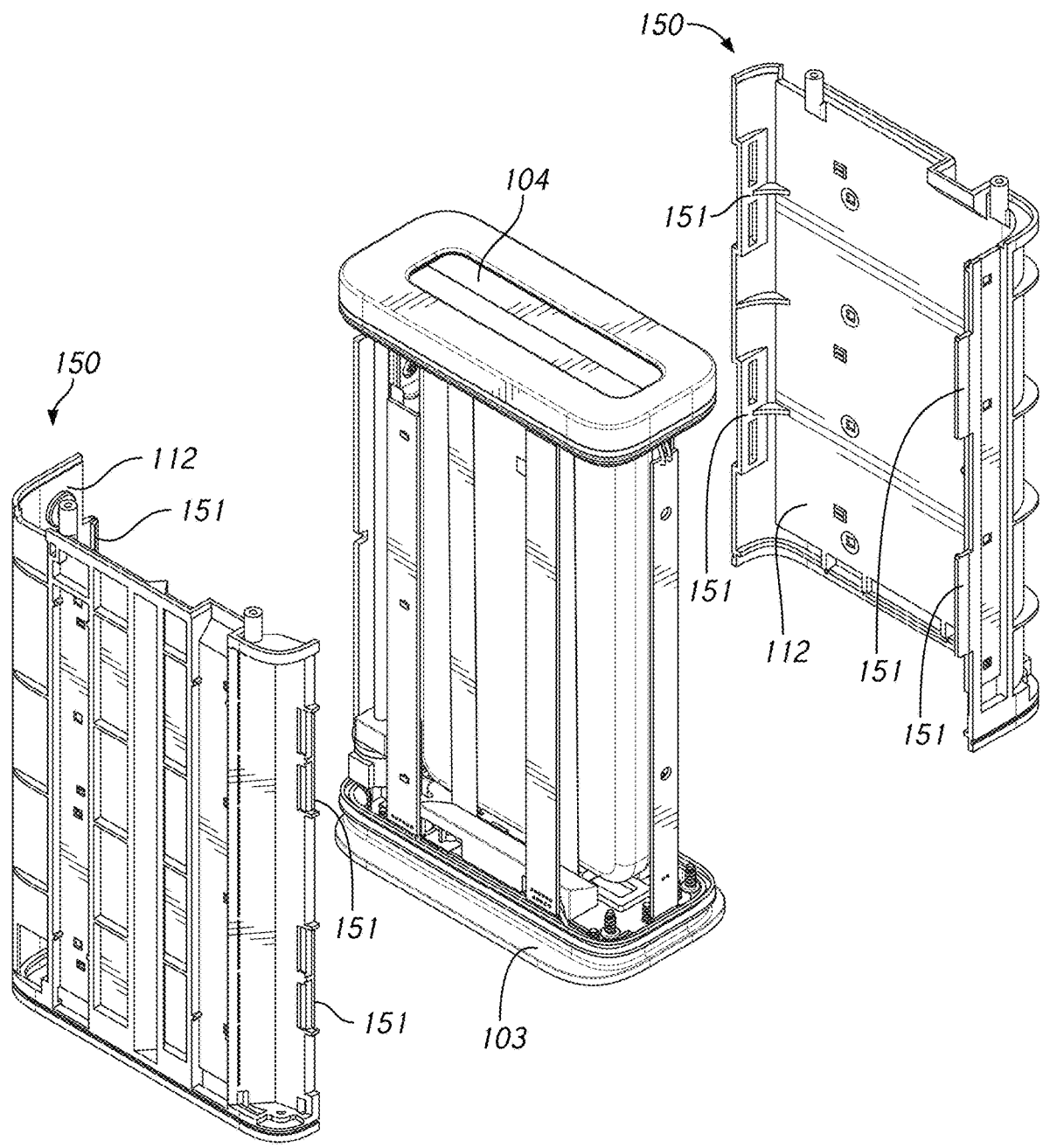
FIG. 20 shows the embodiment of FIGS. 18 and 19, with wall structures separated.

Another example of a sanitizing system 100 is illustrated in FIGS. 18-20. FIG. 18 shows the outer contours of an embodiment of a sanitizing system 100. As shown in FIG. 18, the housing 101 can comprise a height measurement that is substantially larger than its width or depth measurements. In some embodiments, the dimensions of the housing 101 (e.g., width, depth, and/or height) can each be no more than about 20% larger or no more than about 50% larger than each of the dimensions of the types of mobile electronic devices that are intended to be sanitized by the sanitizing system 100.

The housing 101 can comprise a base 103 positioned at the bottom of the housing. As shown, the base 103 can comprise a width and/or depth that is larger than the width and/or depth of the portion of the housing above the base 103 to provide increased stability by resisting tipping or wobbling as a mobile electronic device is inserted into or withdrawn from the sanitizing system 100. The portion of the housing above the base 103 can gradually decrease in width and/or depth to create a curved or smooth appearance, as shown in FIG. 18. The enclosure 104 can be located in a non-flush recessed position with respect to an upper portion of the housing 101.

The housing 101 of the sanitizing system 100 comprises an enclosure with six sides: a top, a bottom, a left side, a right side, a front side, and a rear side. As shown, the opening to receive and eject the mobile electronic device 200 is provided on only a single side. The opening can be provided on any single side or can span multiple sides. In some embodiments in which the opening is provided on only a single side, the interior of the sanitizing system 100 can be maintained in a more sanitary, debris-free, and otherwise protected condition than when the entire interior of the housing is exposed when opening up and inserting or retrieving the mobile electronic device 200 from within the sanitizing system 100, such as in a hinged clam-shell type housing arrangement where a user's fingers are likely to touch the interior of the sanitizing system 100.

In the illustrated embodiments, the housing 101 can remain generally or substantially closed even when the mobile electronic device 200 is inserted or ejected from the housing 101, by virtue of the single-side opening and the closeable opening with the outer enclosure 104. In some embodiments, as shown, the user's experience with the device is made easier by permitting the user to simply activate the sanitizing system 100 by pushing a mobile electronic device 200 into the single-side opening and retrieving the mobile electronic device 200 from the same single-side opening when the sanitizing process is complete and the mobile electronic device 200 is ejected, without requiring the user to manually open the housing 101, precisely position the mobile electronic device 200 within the cavity of the housing 101, and/or manually close the housing 101.

FIG. 19 shows the embodiment of FIG. 18, with an outer cover removed to reveal structural features. The embodiment can include wall structures 150. The wall structures 150 can comprise two parts, as shown in FIG. 20. While two wall structures 150 are illustrated, any number of wall structures 150 can be used. For example, 1, 2, 3 or more wall structures 150. The wall structures 150 provide support for the sanitizing system 100 and can protect the interior features. FIG. 20 shows the same embodiment, with wall structures 150 separated to reveal additional interior features. For example, FIG. 20 illustrates the radiation-emitting sources 114 and the one or more sanitizing panels 112. In some embodiments, the wall structures 150 can be coupled via overlapping pieces 151. The overlapping pieces 151 can include corresponding recesses and protrusions as shown. Other suitable coupling methods can also be used for coupling the wall structures 150. The wall structures 151 can be positioned between the first outer enclosure 104 and the base 103.

Figure 21:
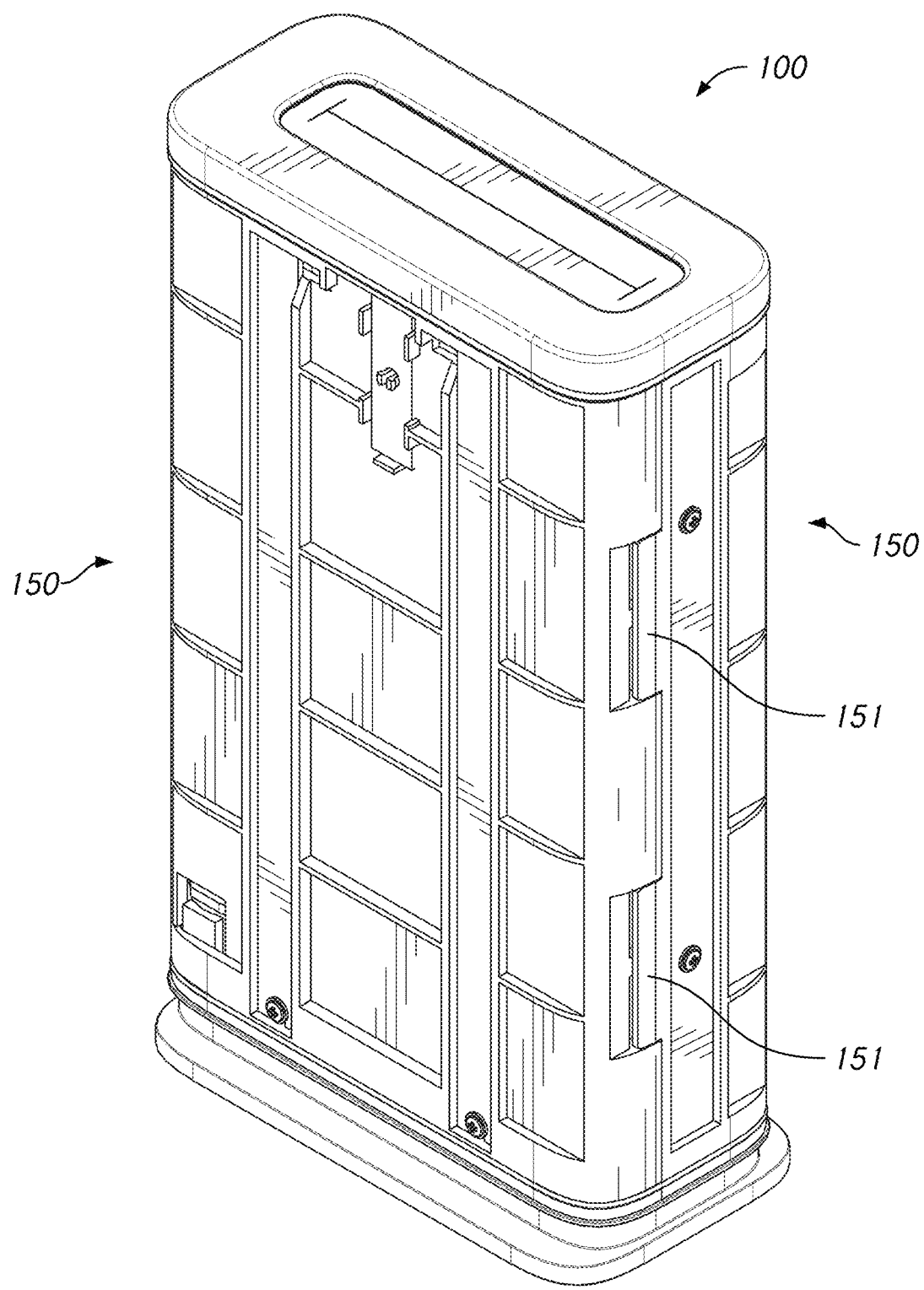
FIG. 21 shows a perspective view of the embodiment of FIG. 8, with an outer cover removed.
Figure 22:
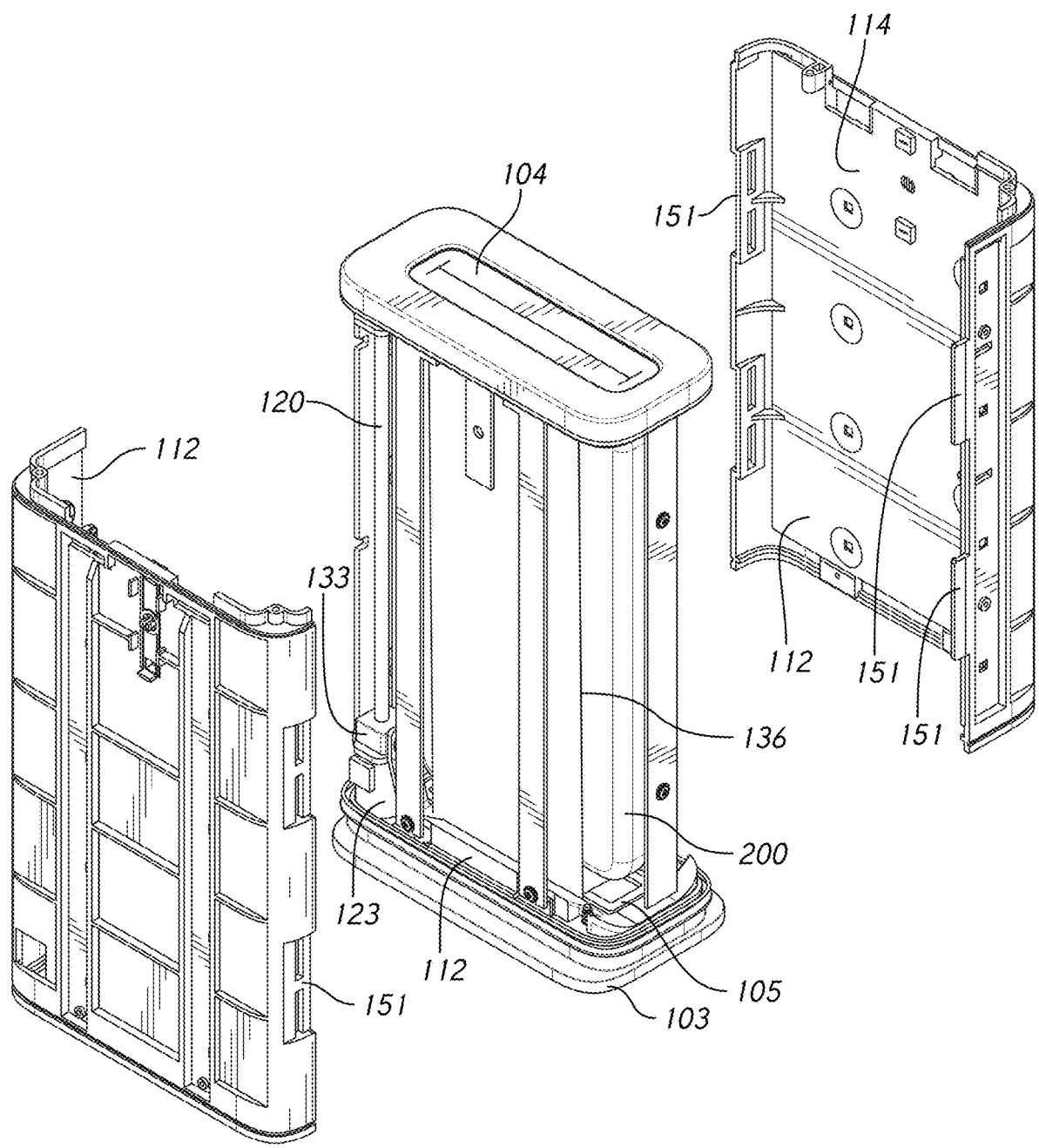
FIG. 22 shows the embodiment of FIGS. 8 and 21 with wall structures separated.
Figure 23:
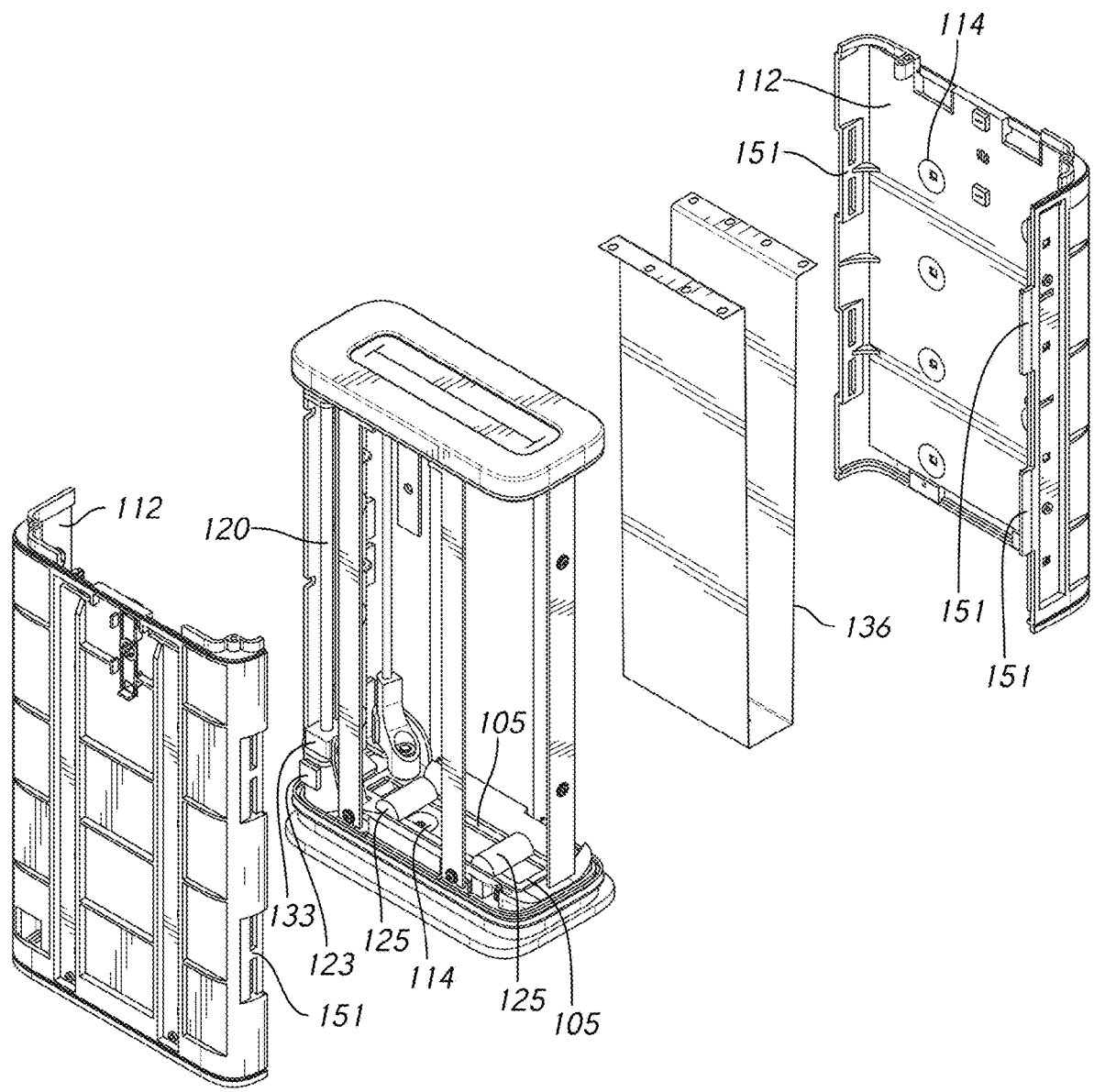
FIG. 23 shows an interior view of the embodiment of FIGS. 8, 21, and 22, separating additional interior features.

FIG. 21 shows the embodiment of FIG. 8 with an outer cover removed to reveal structural features. The embodiment can include wall structures 150. The wall structures 150 can comprise two parts, as shown in FIGS. 22 and 23. While two wall structures 150 are illustrated, any number of wall structures 150 can be used. For example, 1, 2, 3 or more wall structures 150. The wall structures 150 provide support for the sanitizing system 100 and can protect the interior features. In some embodiments, the wall structures 150 can be coupled via overlapping pieces 151. The overlapping pieces 151 can include corresponding recesses and protrusions as shown in FIGS. 22 and 23. Other suitable coupling methods can also be used for coupling the wall structures 150. The wall structures 151 can be positioned between the first outer enclosure 104 and the base 103.

Figure 24:
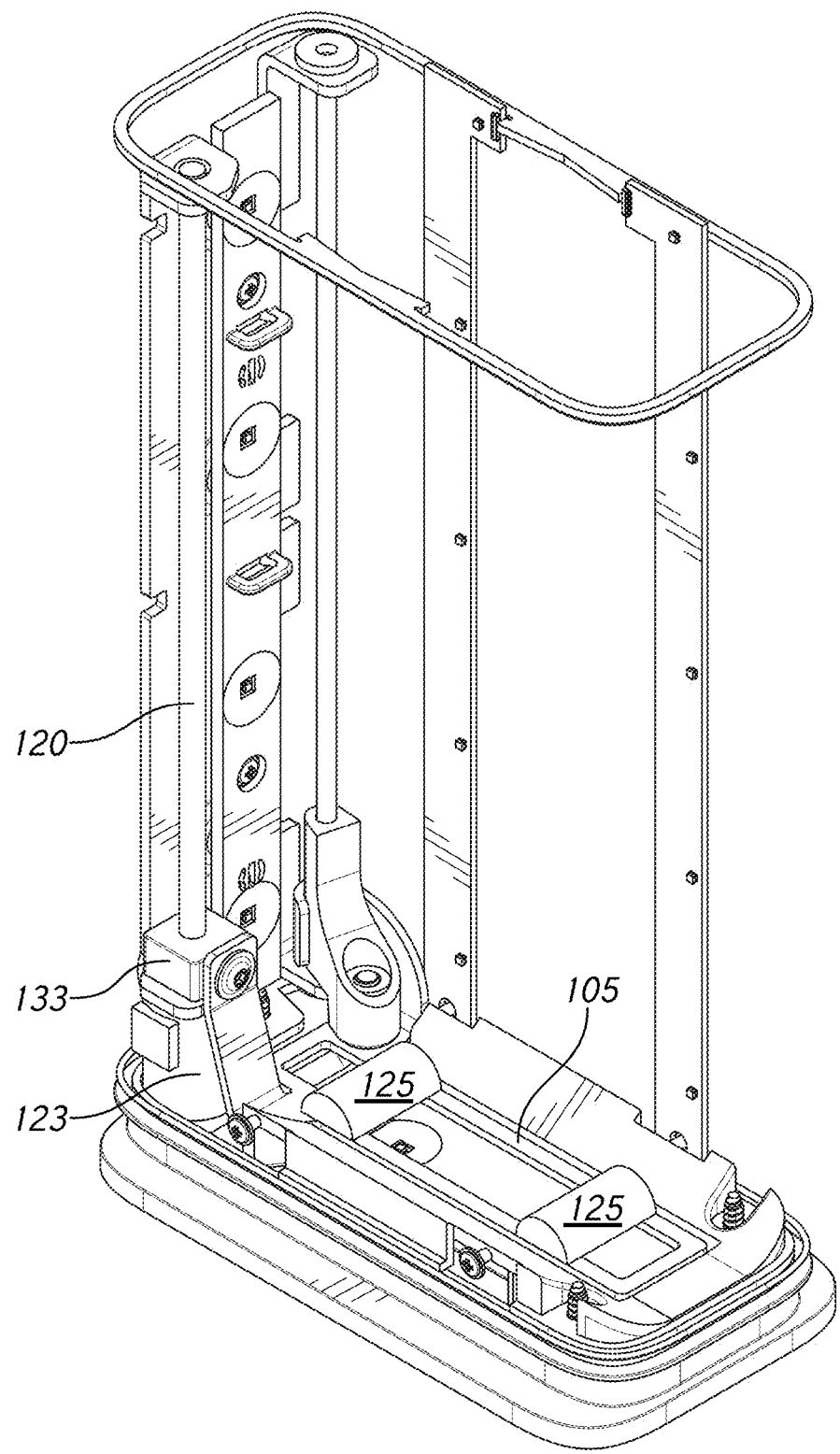
FIG. 24 shows an interior view of the embodiment of FIGS. 8, 21, 22, and 23, removing obstructing features.

FIG. 22 shows the same embodiment, with wall structures separated to reveal additional interior features (including a phone visible inside the device). FIG. 23 shows the same embodiment and further separates additional interior features and removes the phone. FIGS. 22 and 23 shows some of the features described in FIG. 9, such as the cradle 136, the carriage 105, one or more contact surfaces 125, the radiation-emitting sources 114, the carriage rider 133, the electric motor 123, the conveyor 120, and the one or more sanitizing panels 112. FIG. 24 further removes obstructing features to provide a more direct view of some of the features described in FIG. 9 such as the conveyor 120 in the form of a threaded post, the carriage 105, the carriage rider 133, the electric motor 123, and contact surfaces 125.

In any embodiment of this specification, when the mobile electronic device 200 is positioned in the interior space of the sanitizing system 100, the mobile electronic device 200 can be exposed to a sanitizing process such as an irradiation process using electromagnetic radiation. In some embodiments, the sanitizer of the sanitizing system 100 is configured to kill at least about 90%, at least about 97%, or at least about 99% of the microbes that actually reside on, or that are commonly known to reside on, the outer surface of a mobile electronic device 200, within a single cycle of sanitizing. In some embodiments, a cycle of sanitizing can be completed within about 30 seconds or less, or within about 45 seconds or less, or within about 1 minute or less. During the cycle, the one or more radiation sources can be configured to emit a suitable type of radiation or range or band of radiation, including any type of radiation described elsewhere in this specification, continuously or intermittently. In some embodiments, while the one or more radiation-emitting sources 114 are emitting radiation, either or both of the receiver system or the one or more sanitizing panels 112 supporting the radiation-emitting sources 114 can be configured to produce relative movement between the mobile electronic device 200 and the one or more radiation-emitting sources to help accomplish a generally uniform irradiation or application of sanitizing effect across substantially the entire outer surface of the mobile electronic device 200. The relative movement may be generally vertical movement, generally horizontal movement, generally circular movement, or any combination of the foregoing or otherwise.

In some embodiments, during the time that the carriage 105 is moving the mobile electronic device 200 downward or upward into or out of the housing 101, the radiation-emitting sources 114 can be activated by the processor 121 to emit radiation. The processor can cause the carriage 105 to pause one or more times at one or more particular positions that correspond to one or more regions of relatively higher irradiation intensity (e.g., at one or more positions where one or more radiation-emitting source 114 emit radiation primarily perpendicularly to a particular region of the mobile electronic device 200) in order to ensure that one or more particular portions of the mobile electronic device 200 are irradiated thoroughly and sufficiently, such as one or more of the top or bottom or side edges, one or more speakers, one or more microphones, one or more buttons that are commonly depressed, and/or any other part of the mobile electronic device 200. The duration of the one or more pauses can be any suitable time, such as at least about 1 second or at least about 1.5 seconds or at least about 2 seconds.

The receiving system can be configured to "overtravel" such that the highest position of one or more radiation-emitting sources 114 within the interior of the sanitizing system 100 is above the highest position of the mobile electronic device 200 when fully received into the cavity of the sanitizing system 100 and/or the lowest position of one or more radiation-emitting sources 114 within the interior of the sanitizing system 100 is above the lowest position of the mobile electronic device 200 when fully received into the cavity of the sanitizing system 100. In some embodiments, essentially all (e.g., at least about 95%) or substantially all (e.g. at least about 80%) of the outer surfaces of the mobile electronic device 200 can be irradiated with at least about 7 $mJ/cm^2$ or at least about 8 $mJ/cm^2$ of radiant exposure or radiation energy-area density by the radiation-emitting sources 114 during a single cycle. In some embodiments, the sanitizing system 100 is effective in killing about 99.9% of common microbes on virtually the entire external surface (e.g., top edge, bottom edge, left and right edges, front and rear faces) of the mobile electronic device 200.

The number and spacing of the radiation-emitting sources 114 on each sanitizing panel 112 or side of the interior of the housing 101 can provide advantages in the evenness, thoroughness, and/or microbial kill-rate of the sanitizing system 100. For example, in some embodiments, the radiation-emitting sources 114 can be spaced apart from each other by at least about 1 cm and/or less than or equal to about 2 cm. In some embodiments, the mobile electronic device 200, when positioned fully within the interior of the housing, is configured to be spaced apart from most or all of the radiation-emitting sources 114 by at least about 0.5 cm and/or less than or equal to about 1 cm. In some embodiments, at least about four, or at least about five, or at least about six radiation-emitting sources 114 are provided vertically and/or horizontally across some or all sides of the mobile electronic device 200.

As illustrated in some examples (see, e.g., FIG. 9), the interior of the housing 101 can include at least one or a plurality of radiation-emitting sources 114 on each of a plurality of side panels 112 (e.g., 2, 3, or 4) that can be positioned at about the same vertical level within the sanitizing system 100. By providing a plurality of radiation-emitting sources 114 at about the same vertical level, the positioning of the mobile electronic device 200, and/or the motion and timing of movement of the mobile electronic device 200 through the sanitizing system 100, can provide generally even, uniform, consistent, and/or controlled coverage on the mobile electronic device 200 by radiation at each of a plurality of approximately the same vertical levels. In the example shown in FIG. 9, at about the same vertical level, two radiation-emitting sources 114 can be provided on each of the wider front and rear side panels 112, and one radiation-emitting sources 114 can be provided on each of the narrower lateral side panels 112, for a total of six radiation-emitting sources 114 at about the same vertical level. As shown, multiple sets of radiation-emitting sources 114 can be provided at a plurality of different approximately equal vertical levels, such as at least two sets on at least two approximately equal vertical levels and/or at least four sets on at least four approximately equal vertical levels. As shown, in some embodiments, at least two sets or at least three sets of a plurality of radiation-emitting sources 114 can be configured to emit radiation in at least two or at least three essentially or substantially perpendicular directions. In some embodiments, at least about 24 total radiation-emitting sources 114 are provided within the sanitizing system 100 or at least about 30 total radiation-emitting sources 114 are provided within the sanitizing system 100. In some implementations, by providing an appropriate pattern of spacing between individual radiation-emitting sources 114 and between the mobile electronic device 200 and the radiation-emitting sources 114, variations in the coverage of radiation across a given area of the mobile electronic device 200 during sanitizing can be diminished and a generally even exposure and high microbial kill-rate can be accomplished.

After treatment or sanitizing of the mobile electronic device 200 in the sanitizing system 100, the mobile electronic device 200 in some embodiments can become substantially or entirely free of living microbes of the type commonly encountered by users of mobile electronic devices 200 that present clinically significant risks or threats to human health. In some embodiments, the sanitizing system 100 is capable of killing a majority of the types of microbes that frequently are present on mobile electronic devices 200 and/or is capable of killing a majority of the individual organisms of the microbes that are present on a particular mobile electronic device 200 when it is inserted into the sanitizing system 100.

In some embodiments, the sanitizing system 100 can be provided next to, in close proximity with, on the same countertop as, or within the same housing as, and/or as part of the same system as, a touch-free soap or antiseptic dispenser. The touch-free dispenser can include a reservoir of soap or antiseptic that is dispensed by a pump upon actuation by a user's hands, such as using a proximity or other type of sensor. A user can insert a mobile electronic device 200 into the sanitizing system 100 at about the same time as, or slightly before or after, a user approaches or actuates the dispenser to receive a usable portion of soap or antiseptic. The user can then clean, wash, or sanitize the user's hands with the dispensed soap or antiseptic while the sanitizing system 100 sanitizes the mobile electronic device 200. In some embodiments, the duration of the sanitizing procedure in the sanitizing system 100 is about the same amount of time as and/or less than or equal to about the average time for sanitizing or cleaning a person's hands.

The invention claimed is:

1. A sanitizing system comprising:
    a housing;
    an entry system configured to permit an electronic device to pass through the entry system and into an interior of the housing;
    a receiver system configured to receive the electronic device that is inserted into the housing, to move the electronic device fully into the interior of the housing, and to move the electronic device at least partially outside of the housing following a sanitizing procedure; and
    a plurality of sanitizing or radiation-emitting sources positioned within the housing and configured to sanitize the electronic device, a first sanitizing or radiation-emitting source of the plurality of sanitizing or radiation-emitting sources positioned at a first height within the housing and a second sanitizing or radiation-emitting source of the plurality of sanitizing or radiation-emitting sources positioned at a second height within the housing, the second height being different than the first height.

2. The sanitizing system of claim 1, wherein the first sanitizing or radiation-emitting source is positioned on a first side of the interior of the housing and wherein the second sanitizing or radiation-emitting source is positioned on a second side of the interior of the housing.

3. The sanitizing system of claim 1, wherein the first sanitizing or radiation-emitting source is positioned at or near a base of the housing.

4. The sanitizing system of claim 1, wherein the plurality of sanitizing or radiation-emitting sources are configured to perform a generally uniform application of a sanitizing effect across substantially an entire outer surface of the electronic device.

5. The sanitizing system of claim 1, wherein the first sanitizing or radiation-emitting source is positioned above a highest position of the electronic device when fully received within the interior of the housing and wherein the second sanitizing or radiation-emitting source is positioned below a lowest position of the electronic device when fully received within the interior of the housing.

6. The sanitizing system of claim 1, wherein the plurality of sanitizing or radiation-emitting sources are positioned vertically and horizontally across sides of the interior of the housing.

7. The sanitizing system of claim 1, wherein a height of the housing exceeds a width and a length of the housing.

8. A sanitizing system comprising:
    a housing;
    an entry system configured to permit an electronic device to pass through the entry system and into an interior of the housing;
    a receiver system configured to receive the electronic device that is inserted into the housing, to move the electronic device fully into the interior of the housing, and to move the electronic device at least partially outside of the housing following a sanitizing procedure; and
    a plurality of sanitizing or radiation-emitting sources positioned within the housing and configured to sanitize the electronic device within about 1 minute or less and kill at least about 90 percent of microbes residing on the electronic device.

9. The sanitizing system of claim 8, wherein the plurality of sanitizing or radiation-emitting sources are configured to sanitize the electronic device within about 45 seconds or less.

10. The sanitizing system of claim 8, wherein the plurality of sanitizing or radiation-emitting sources are configured to sanitize the electronic device within about 30 seconds or less.

11. The sanitizing system of claim 8, wherein the plurality of sanitizing or radiation-emitting sources are configured to kill at least 97 percent of microbes residing on the electronic device.

12. The sanitizing system of claim 8, wherein the plurality of sanitizing or radiation-emitting sources are configured to kill at least 99 percent of microbes residing on the electronic device.

13. The sanitizing system of claim 8, wherein the plurality of sanitizing or radiation-emitting sources are configured to sanitize the electronic device within about 30 seconds and kill at least 99 percent of microbes residing on the electronic device.

14. A sanitizing system comprising:
a housing;
an entry system configured to permit an electronic device to pass through the entry system and into an interior of the housing;
a receiver system configured to receive the electronic device that is inserted into the housing, to move the electronic device fully into the interior of the housing, and to move the electronic device at least partially outside of the housing following a sanitizing procedure;
a plurality of sanitizing or radiation-emitting sources positioned within the housing and configured to sanitize the electronic device; and
a first reflector positioned in a lower region of the housing and configured to reflect sanitizer or radiation emitted from the plurality of sanitizing or radiation-emitting sources generally toward the electronic device.

15. The sanitizing system of claim 14, further comprising a second reflector positioned in the lower region.

16. The sanitizing system of claim 15, wherein the first reflector and the second reflector are positioned on opposite sides of a carriage of the receiver system.

17. The sanitizing system of claim 14, wherein the first reflector comprises a generally concave or parabolic surface.

18. The sanitizing system of claim 14, wherein the first reflector comprises a film or thin sheet of material positioned over a support, and wherein a void or hollow configured to contain additional components is positioned under the support.

19. The sanitizing device of claim 14, wherein the first reflector has a higher outward height and a lower inward height.

20. The sanitizing device of claim 14, wherein the first reflector is configured to assist in centering the electronic device.

* * * * *

UNITED STATES PATENT AND TRADEMARK OFFICE
CERTIFICATE OF CORRECTION

| | | |
|---|---|---|
| PATENT NO. | : 12,274,803 B2 | Page 1 of 1 |
| APPLICATION NO. | : 18/425218 | |
| DATED | : April 15, 2025 | |
| INVENTOR(S) | : Frank Yang | |

It is certified that error appears in the above-identified patent and that said Letters Patent is hereby corrected as shown below:

In the Claims

In Column 24, Claim 19, Line 12 (Approx.), delete "sanitizing device" and insert --sanitizing system--.

In Column 24, Claim 20, Line 15 (Approx.), delete "sanitizing device" and insert --sanitizing system--.

Signed and Sealed this
Seventeenth Day of June, 2025

Coke Morgan Stewart
*Acting Director of the United States Patent and Trademark Office*